United States Patent
Georgescu et al.

(10) Patent No.: US 9,730,643 B2
(45) Date of Patent: *Aug. 15, 2017

(54) METHOD AND SYSTEM FOR ANATOMICAL OBJECT DETECTION USING MARGINAL SPACE DEEP NEURAL NETWORKS

(71) Applicant: Siemens Healthcare GmbH, Erlangen (DE)

(72) Inventors: Bogdan Georgescu, Plainsboro, NJ (US); Yefeng Zheng, Princeton Junction, NJ (US); Hien Nguyen, Princeton, NJ (US); Vivek Kumar Singh, Monmouth Junction, NJ (US); Dorin Comaniciu, Princeton Junction, NJ (US); David Liu, Franklin Park, NJ (US)

(73) Assignee: Siemens Healthcare GmbH, Erlangen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/055,161

(22) Filed: Feb. 26, 2016

(65) Prior Publication Data

US 2016/0174902 A1 Jun. 23, 2016

Related U.S. Application Data

(63) Continuation-in-part of application No. 14/709,536, filed on May 12, 2015, now Pat. No. 9,668,699, and
(Continued)

(51) Int. Cl.
*A61B 5/00* (2006.01)
*G06T 7/00* (2017.01)
(Continued)

(52) U.S. Cl.
CPC .......... *A61B 5/7267* (2013.01); *A61B 6/5217* (2013.01); *A61B 8/5223* (2013.01);
(Continued)

(58) Field of Classification Search
CPC ....... A61B 6/503; A61B 6/507; A61B 6/5217; A61B 6/563; A61B 8/0883; A61B 8/0891;
(Continued)

(56) References Cited

U.S. PATENT DOCUMENTS

| 8,700,552 B2 | 4/2014 | Yu et al. |
| 2008/0085050 A1* | 4/2008 | Barbu ................. G06K 9/6292 382/154 |

(Continued)

FOREIGN PATENT DOCUMENTS

WO 2014072861 A3 5/2014

OTHER PUBLICATIONS

Bengio et al. 2012, Unsupervised Feature Learning and Deep Learning: A Review and New Perspectives, Jun. 24, 2012.*
(Continued)

*Primary Examiner* — Bo J Peng

(57) ABSTRACT

A method and system for anatomical object detection using marginal space deep neural networks is disclosed. The pose parameter space for an anatomical object is divided into a series of marginal search spaces with increasing dimensionality. A respective sparse deep neural network is trained for each of the marginal search spaces, resulting in a series of trained sparse deep neural networks. Each of the trained sparse deep neural networks is trained by injecting sparsity into a deep neural network by removing filter weights of the deep neural network.

42 Claims, 26 Drawing Sheets

Related U.S. Application Data a continuation-in-part of application No. 14/516,163, filed on Oct. 16, 2014.

(60) Provisional application No. 62/121,527, filed on Feb. 27, 2015, provisional application No. 62/121,782, filed on Feb. 27, 2015, provisional application No. 62/148,273, filed on Apr. 16, 2015, provisional application No. 61/891,920, filed on Oct. 17, 2013.

(51) Int. Cl.

| | | |
|---|---|---|
| G06K 9/46 | (2006.01) | |
| G06K 9/62 | (2006.01) | |
| G06T 7/73 | (2017.01) | |
| A61B 6/00 | (2006.01) | |
| A61B 8/08 | (2006.01) | |
| A61B 8/00 | (2006.01) | |
| A61B 5/055 | (2006.01) | |

(52) U.S. Cl.
CPC ......... *G06K 9/4628* (2013.01); *G06K 9/6255* (2013.01); *G06T 7/0012* (2013.01); *G06T 7/73* (2017.01); *A61B 5/055* (2013.01); *A61B 6/503* (2013.01); *A61B 6/507* (2013.01); *A61B 6/563* (2013.01); *A61B 8/0883* (2013.01); *A61B 8/0891* (2013.01); *A61B 8/565* (2013.01); *G06K 2209/051* (2013.01); *G06T 2200/04* (2013.01); *G06T 2207/10072* (2013.01); *G06T 2207/10132* (2013.01); *G06T 2207/20016* (2013.01); *G06T 2207/20024* (2013.01); *G06T 2207/20081* (2013.01); *G06T 2207/20084* (2013.01); *G06T 2207/30048* (2013.01); *G06T 2207/30101* (2013.01)

(58) Field of Classification Search
CPC ....... A61B 8/5223; A61B 8/565; A61B 5/055; G06K 2009/4666; G06K 2209/051; G06T 2207/10081; G06T 2207/10088; G06T 2207/10101; G06T 2207/10132; G06T 2207/20081; G06T 2207/20084; G06T 2207/30048

See application file for complete search history.

(56) References Cited

U.S. PATENT DOCUMENTS

| | | | |
|---|---|---|---|
| 2012/0232386 A1* | 9/2012 | Mansi | A61B 8/0883 600/437 |
| 2013/0138436 A1 | 5/2013 | Yu et al. | |
| 2013/0138589 A1 | 5/2013 | Yu et al. | |
| 2014/0072213 A1* | 3/2014 | Paiton | G06K 9/4619 382/165 |
| 2014/0100451 A1 | 4/2014 | Tolkowsky et al. | |
| 2015/0112182 A1 | 4/2015 | Sharma et al. | |
| 2015/0125049 A1 | 5/2015 | Taigman et al. | |
| 2015/0161987 A1 | 6/2015 | Horesh et al. | |
| 2015/0161988 A1 | 6/2015 | Dognin et al. | |
| 2015/0170002 A1 | 6/2015 | Szegedy et al. | |
| 2015/0238148 A1 | 8/2015 | Georgescu et al. | |
| 2015/0245775 A1 | 9/2015 | Fonte et al. | |

OTHER PUBLICATIONS

Deng, Three Classes of Deep Learning Architectures and Their Applications: A Tutorial Survey, APSIPA Transactions of Signal and Information Processing, 2012, 28 pages.

Krizhevsky et al., ImageNet Classification with Deep Convolutional Neural Networks, , Conference: Advances in Neural Information Processing Systems 25, 2012, pp. 1-9.

\* cited by examiner

FIG. 15

| | | |
|---|---|---|
| 1502 → | 1: | Pre-training using all weights $w^{(0)} \leftarrow w$ (small # epochs) |
| 1504 → | 2: | Initialize sparsity map $s^{(0)}$ with ones |
| | 3: | $t \leftarrow 1$ |
| | 4: | for training round $t \leq T$ do |
| | 5: |     for all filter $i$ with sparsity do |
| 1506 → | 6: |         $s_i^{(t)} \leftarrow s_i^{(t-1)}$ + remove smallest active weights |
| | 7: |         $w_i^{(t)} \leftarrow w_i^{(t-1)} \odot s_i^{(t)}$ |
| 1508 → | 8: |         Normalize active coeff. s.t. $\left\|w_i^{(t)}\right\|_1 = \left\|w_i^{(t-1)}\right\|_1$ |
| 1510 → | 9: |     end for |
| | 10: |     $b^{(t)} \leftarrow b^{(t-1)}$ (copy current biases) |
| 1512 → | 11: |     Train network on active weights (small # epochs) |
| | 12: |     $t \leftarrow t + 1$ |
| | 13: | end for |
| 1514 → | 14: | Sparse kernels: $w_s \leftarrow w^{(T)}$ |
| | 15: | Biases: $b_s \leftarrow b^{(T)}$ |

1602 → 1:  Set iteration count $l$ in optimization cycle to zero, $\lambda_i^{(0)} = 1, i = 1, ..., N$
1604 → 2:  Estimate $w^{(l)}$ using gradient backpropagation step
1606 → 3:  Update coefficients of regularization term: $\lambda_i^{(l+1)} = \frac{1}{\|w_i^{(l)}\| + \epsilon}$
       4:  Terminate on convergence / maximum number of iterations; otherwise increment iteration count $l$ and return to 2.

```
         1:    P - set of positive samples
         2:    N - set of negative samples (|P| ≪ |N|)
2002     3:    while |N| ≥ 1.5 × |P| do
         4:        Train shallow sparse neural network
2004     5:        d ← largest decision boundary with FNR = 0
2006     6:        Filter N based on d – eliminate true negatives
         7:    end while
```

METHOD AND SYSTEM FOR ANATOMICAL OBJECT DETECTION USING MARGINAL SPACE DEEP NEURAL NETWORKS

This application claims the benefit of U.S. Provisional Application No. 62/121,527, filed Feb. 27, 2015, and U.S. Provisional Application No. 62/121,782, filed Feb. 27, 2015, and is a continuation-in-part of U.S. application Ser. No. 14/709,536, which claims the benefit of U.S. Provisional Application No. 62/148,273, filed Apr. 16, 2015, and U.S. Provisional Application No. 62/121,782, filed Feb. 27, 2015, and is a continuation-in-part of U.S. application Ser. No. 14/516,163, filed Oct. 16, 2014, which claims the benefit of U.S. Provisional Application No. 61/891,920, filed Oct. 17, 2013, the disclosures of which are all herein incorporated by reference.

BACKGROUND OF THE INVENTION

The present invention relates to anatomical object detection in medical image data, and more particularly, to anatomical object detection in medical image data using deep neural networks.

Fast and robust anatomical object detection is a fundamental task in medical image analysis that supports the entire clinical imaging workflow from diagnosis, patient stratification, therapy planning, intervention, and follow-up. Automatic detection of an anatomical object is a prerequisite for many medical image analysis tasks, such as segmentation, motion tracking, and disease diagnosis and quantification. Marginal space learning (MSL) was previously introduced to address the problem of anatomy detection and tracking in medical images, such as computed tomography (CT), magnetic resonance (MR), ultrasound, and fluoroscopic images. MSL is an efficient discriminative learning framework that typically uses handcrafted image features extracted from training images to train discriminative classifiers for anatomical object detection in a supervised manner. MSL works well for detecting anatomical structures in various two-dimensional (2D) and three-dimensional (3D) medical imaging modalities. However, anatomical object detection using MSL is not always robust, especially for some challenging detection problems in which the anatomical objects exhibit large variations in anatomy, shape, or appearance in the medical images

BRIEF SUMMARY OF THE INVENTION

The present disclosure provides methods and systems for anatomical object detection using marginal space deep neural networks. Embodiments of the present invention divide a parameter space of a target anatomical object into a series of marginal search spaces with increasing dimensionality. A respective deep neural network is trained for each of the marginal search spaces based on annotated training data. Instead of using handcrafted image features, each of the deep neural networks directly inputs image patches from the training data and learns high-level domain-specific image features. The trained deep neural network for a particular marginal search space may be discriminative, in that it calculates, for a given hypothesis in the search space, a probability that the hypothesis in the search space is correct, or may provide a regression function (regressor) that calculates, for each hypothesis in the search space, a difference vector from that hypothesis to predicted pose parameters of the object in the search space. Once the series of deep neural networks is trained, the trained deep neural networks can be applied to an input medical image to detect the target anatomical object in the input medical image.

In one embodiment, a 3D medical image of a patient including a target anatomical object is received. A 3D pose of the target anatomical object is detected in the 3D medical image in a series of marginal parameter spaces of increasing dimensionality using a respective trained sparse deep neural network for each of the marginal search spaces.

In another embodiment, a plurality of landmark candidates for a target anatomical image are detected in the 3D medical image using an initial shallow neural network detector. Deeply learned features are calculated for each of the plurality of landmark candidates using a trained deep neural network. The target anatomical landmark is detected in the 3D medical image from the plurality of landmark candidates based on the deeply learned features for each of the plurality of landmark candidates and other image-based features extracted from the 3D medical image using a trained classifier.

BRIEF DESCRIPTION OF THE DRAWINGS

FIG. 15 illustrates an algorithm for training a sparse adaptive deep neural network (SADNN) using iterative threshold enforced sparsity according to an embodiment of the present invention;

DETAILED DESCRIPTION

Figure 1:
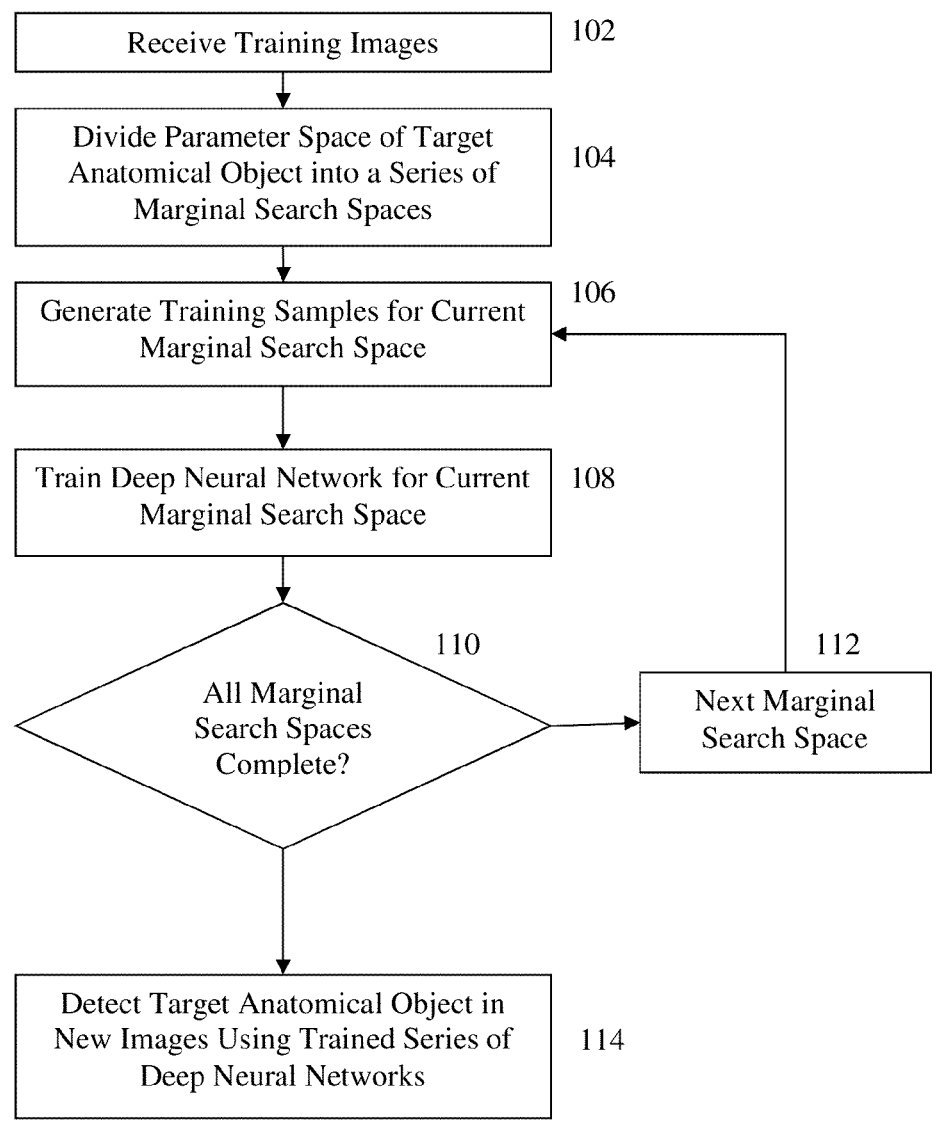
FIG. 1 illustrates a method of training a series of deep neural networks for anatomical object detection in medical images according to an embodiment of the present invention.

The present invention relates to methods and systems for anatomical object detection using marginal space deep neural networks. Embodiments of the present invention are described herein to give a visual understanding of the machine learning based methods for anatomical object detection. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Marginal Space Learning (MSL) is an efficient discriminative learning framework that can be used for anatomical object detection and tracking in medical images, such as but not limited to computed tomography (CT), magnetic resonance imaging (MRI), ultrasound, and X-ray fluoroscopy. MSL exploits large image databases with expert annotations to train discriminative classifiers in a supervised manner on marginal feature distributions from positive (object) and negative (non-object) training samples. Classifiers are sequentially trained by gradually increasing the dimensionality of the search space and focusing only on positive distribution regions. MSL efficiently deals with the problem of an exponentially increasing number of hypotheses relative to the dimensionality of the parameter space. Given a new image the input parameter space is sequentially searched with the trained classifiers to find the correct anatomical object location. MSL is typically implemented using handcrafted image features, such as Haar wavelet features for object position estimation and steerable features for position-orientation estimation and position-orientation-scale estimation. Even though such features are efficient, their classification power is weak. MSL relies on boosting technology, for example using a probabilistic boosting tree (PBT), to integrate a large number of weak features into a strong classifier. Although MSL works well for detecting many anatomical structures in various 2D or 3D medical imaging modalities, when the appearance of an anatomical object is complex relative to the parameter space or when there is a large degree of ambiguity between the background and the anatomical object of interest, there are still problems in capturing these distributions in the discriminative MSL framework with the standard image features.

Embodiments of the present invention utilize deep neural networks trained directly on the image data instead of handcrafted features extracted from the image data to learn complex image patterns and detect anatomical objects based on the complex image patterns. Deep neural networks are machine learning based neural networks with multiple hidden layers of learned features or variables between the input data and the output data. Deep neural networks will typically be implemented with three or more hidden layers. Deep neural networks are typically used in direct multi-class classification scenarios and are not typically applied to anatomical object detection tasks because the extension of deep neural networks to the task of anatomical object detection can be quite computationally complex due to the need to scan a large image parameter space, especially for large 2D+time or 3D volumetric images. Embodiments of the present invention provide computationally efficient methods for utilizing deep neural networks for anatomical object detection in medical images.

FIG. 1 illustrates a method of training a series of deep neural networks for anatomical object detection in medical images according to an embodiment of the present invention. The method of FIG. 1 utilizes a database of training images to train a series of deep neural networks in a series of marginal search spaces of increasing dimensionality to determine a full pose parameter space for an anatomical object in a medical image. In a possible implementation, the method of FIG. 1 can train each of the deep neural networks to be discriminative in that it calculates, for a given hypothesis in a search space, a probability that the hypothesis in the search space is correct. In another possible implementation, the method of FIG. 1 can train each of the deep neural networks to be a regression function (regressor) that calculates, for each hypothesis in a search space, a difference vector from that hypothesis to predicted pose parameters of the target anatomical object in the search space. It is also possible, the one or more of the deep neural networks can be discriminative and one or more of the deep neural networks can be a regressor.

Referring to FIG. 1, at step 102, training images are received. In particular, a plurality of training images are loaded from a database. The training images can be 2D or 3D medical images acquired using any medical imaging modality, such as but not limited to CT, MRI, Ultrasound, X-ray fluoroscopy, DynaCT, etc. At least a subset of the training images are annotated with the pose (e.g., position, orientation, and scale) of the target anatomical object. The training images may also include non-annotated images as well.

At step 104, a parameter space of the target anatomical object is divided into a series of marginal search spaces. The target object annotated in the training images is parameterized and the parameter space of the target anatomical object is divided into a series of marginal search spaces with increasing dimensionality. For example, a set of parameters for a target anatomical object can be the rigid position (translation), orientation (rotation), and scale defining the pose of the object in an image, and the parameter space of the target anatomical object can be divided into marginal search spaces of position, postion+orientation, and position+orientation+scale. A range for each of the parameter spaces is determined from the annotated training images. The parameter space for the target object in 2D images has five degrees of freedom (two for position, one for orientation, and two for anisotropic scaling), while the parameter space for the target object in 3D images has nine degrees of freedom (three for position, three for orientation, and three for anisotropic scaling). For 2D images, the full parameter space can be expressed as $(x,y,\theta,s_x,s_y)$, where $(x,y)$ denotes a center position of the target anatomical object, $\theta$ denotes an orientation or rotation of the anatomical object, and $(s_x, s_y)$ denotes of scale of the anatomical object in the x and y directions, and the parameter space can be divided into the following marginal search spaces: $(x,y)$, $(x,y,\theta)$, and $(x,y,\theta, s_x,s_y)$. For 3D images, the full parameter space can be expressed as $(x,y,z,\theta_x,\theta_y,\theta_z,s_x,s_y,s_z)$, where $(x,y,z)$ denotes a center position of the target anatomical object, $(\theta_x,\theta_y,\theta_z)$ denotes the orientation of the anatomical object, and $(s_x,s_y, s_z)$ denotes of scale of the anatomical object, and the parameter space can be divided into the following marginal search spaces: $(x,y,z)$, $(x,y,z,\theta_x,\theta_y,\theta_z)$, and $(x,y,z,\theta_x,\theta_y,\theta_x,s_x, s_y, s_z)$. Instead of training a deep neural network to directly detect the target object in the full parameter space, the method of FIG. 1 sequentially trains a series of deep neural networks to detect the parameters of the target anatomical object by training a respective deep neural network in each of the marginal search spaces.

At step 106, training samples are generated for the current marginal search space. The training samples are image patches that are used as hypotheses in the current search space to train the deep neural network for that search space. For the first search space (e.g., position) the training samples are generated by selecting image patches from the training images. For training a discriminative deep neural network, ground truth image patches for the first search space are selected as positive training samples and random non-ground-truth image patches are selected as negative training samples. For example, in the case in which the first marginal search space is the position of the target anatomical objects, image patches centered at the ground truth center position of the target anatomical object in each annotated training image are selected as positive training samples and one or more random image patches located more than a predetermined distance (e.g., 5 mm) from the ground truth center position of the target anatomical object are randomly selected from each annotated training image as the negative training samples. For training the deep neural network as a regressor, the training samples (hypotheses) for the first search space are image patches selected from the range of the first search space in the training images. For subsequent marginal search spaces, the training samples for the current search space are generated by evaluating training samples from the preceding search space using the trained deep neural network for the preceding search space to determine a number of candidates in the preceding search space, and then augmenting the candidates selected by the trained deep neural network in the preceding search space with the additional parameters of the current search space sampled from a range of the current search space in the training images.

At step 108, a deep neural network is trained for the current marginal search space. In a possible embodiment, the deep neural network for the current search space may be a discriminative deep neural network that image patches of an image as hypotheses and for each image patch calculates a probability the parameters of the image patch for the current search space are the parameters for the target anatomical object in the current search space. In another possible implementation, the first deep neural network may train a regressive function that inputs image patches of an image as hypotheses and calculates a difference vector for each input image patch between the parameters of the image patch in the current search space and the parameters of the target anatomical object in the current search space, resulting in predicted parameters of the target anatomical object in the current search space.

At step 110, it is determined if the training for all marginal search spaces is complete. If the training for all of the marginal search spaces is not complete, the method proceeds to step 112. If the training for all of the marginal search spaces is complete the method proceeds to step 114. At step 112, the method proceeds to the next marginal search space and then returns to step 106 and repeats steps 106, 108, and 110. In particular, when the method returns to step 106, the hypotheses in the previous search space are evaluated using the deep neural network trained for the previous search space to determine candidates in the previous search space, and training samples (hypotheses) for the next search space are generated by augmenting the candidates in the previous search space with additional parameters for the next search space. The deep neural network for the next search space is then trained, and these steps are repeated until a respective deep neural network is trained for each of the marginal search spaces. The final deep neural network will detect the anatomical object in the full parameter space. For example, steps 108 and 110 can be repeated to train a first deep neural network to detect the position of a target anatomical object, train a second deep neural network to detect position and orientation of the target anatomical object, and train a third deep neural network to detect position, orientation, and scale of the anatomical object. At step 114, once the training is complete for all of the marginal spaces, the series of trained deep neural networks can be used to detect an anatomical object in a new image. Steps 102-112 can be performed offline in a training stage and then the series of trained deep neural networks can be stored in a memory or storage of a computer system, and step 114 can be performed when a new image is received using the stored series of trained deep neural networks. When a new image is received, anatomical object detection can be performed by inputting image patches of the new image into the first trained deep neural network and then processing the image patches sequentially through the series of trained deep neural networks.

Figure 2:
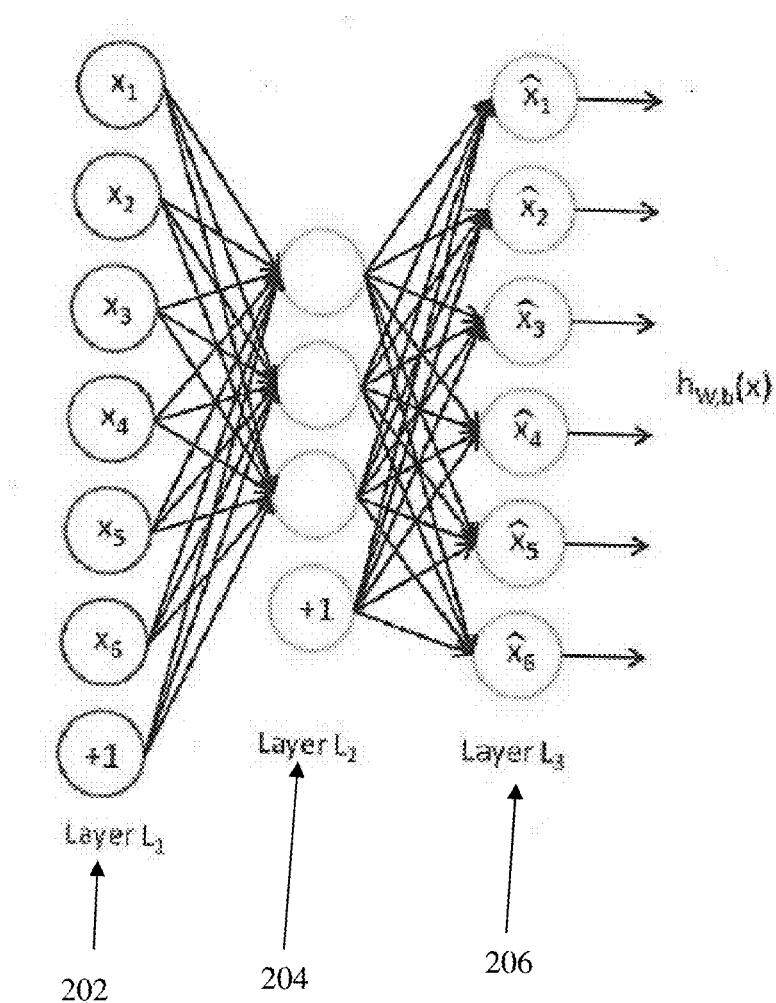
FIG. 2 illustrates an exemplary auto-encoder neural network.

In a first embodiment, the method of FIG. 1 can be used to train a series of discriminative deep neural networks, each of which calculates, for a given hypothesis in its marginal search space, a probability that the hypothesis in the search space is correct. This framework for training a sequential series of discriminative deep neural networks in a series of marginal spaces of increasing dimensionality can be referred to as Marginal Space Deep Learning (MSDL). In MSDL, deep learning is utilized to automatically learn high-level domain-specific image features directly from the medical image data. A feed-forward neural network is a neural network structure with an efficient training algorithm called back-propagation. Although powerful enough to approximate complicated target functions, a large feed-forward neural network tends to over-fit the training data. It is difficult to train a network with more than two hidden layers with good generalization capability. In a possible embodiment, unsupervised pre-training followed by supervised fine-tuning can be used to overcome the over-fitting issue. This technique can be used to train networks with three or more hidden layers. The pre-training can be treated as an unsupervised learning process to discover powerful image features from the input image data. Various deep learning techniques, such as an auto-encoder (AE) or a restricted Boltzman machine (RBM), can be used to pre-train a hidden layer. FIG. 2 illustrates an exemplary AE neural network. As shown in FIG. 2, the AE 200 is a feed-forward neural network with one hidden layer 204. The AE 200 has an input layer $L_1$ 202, the hidden layer $L_2$, and an output layer $L_3$ 206. If the AE 200 is a fully connected network, each node in the input layer 202 can correspond to a respective voxel or pixel of an image patch. Ignoring the bias term (the nodes labeled as +1 in FIG. 2), the input and output layers 202 and 206, respectively have the same number of nodes. The goal of an AE is to minimize the difference between the input and output vectors. If the hidden layer 204 has a size equal to or larger than the input layer 202, an AE may learn an identify transformation. To prevent such a trivial solution, an AE can be set up with a hidden layer 204 with fewer nodes than the input layer 202. The nodes of the hidden layer 204 can be calculated as a function of a bias term and a weighted sum of the nodes of the input layer 202, where a respective weight is assigned to each connection between a node of the input layer 202 and a node in the hidden layer 204. The bias term and the weights between the input layer 202 and the hidden layer 204 are learned in the training of the AE 200, for example using a back-propagation algorithm.

A denoising auto-encoder (DAE) may be used to learn a more meaningful representation of the input image data. In a DAE, a certain percentage (e.g., 50%) of the input nodes are randomly selected to be disturbed (e.g., set the value equal to zero) and the DAE is required to reconstruct the original input vector given a contaminated observation. The hidden layer in a DAE may have more nodes than the input layer to achieve an over-complete representation. According to an advantageous embodiment, in order to train the discriminative deep neural network for a particular marginal search space (step 108 of FIG. 1), after training an AE (or DAE), the output layer is discarded and another AE (or DAE) is stacked using the activation response of the already trained hidden layer as input to the new AE (or DAE). This process can be repeated to train and expand a network layer by layer. In a possible implementation, after pre-training a number of hidden layers, the output of the hidden layers can be treated as high-level image features and used to train a discriminative classifier for detecting the anatomical object in the current parameter space. Alternatively, an additional layer for the target output can be added to the network and the whole network can be refined using back-propagation.

As described above, the method of FIG. 1 uses deep neural networks to train pose classifiers in a series of marginal search spaces for anatomical object detection in medical image data (step 108 of FIG. 1). According to an advantageous implementation, a stacked denoising auto-encoder (DAE) can be used to train one or more of the discriminative classifiers. However, the present invention is not limited to this particular type of deep neural network and other types of deep neural networks, such as a convolutional neural network (CNN), stacked RBM, or a sparse AE, can also be used to train a discriminative classifier.

In a second embodiment, the method of FIG. 1 can use deep neural networks to train a series of regressors, each of which calculates, for each hypothesis in the search space, a difference vector from that hypothesis to predicted pose parameters of the object in the search space. This framework for training a sequential series of deep neural network regressors in a series of marginal spaces of increasing dimensionality can be referred to as Marginal Space Deep Regression (MSDR). In MSDR, a mapping function is learned from the current hypothesis parameters to the correct object parameters in each marginal search space. The mapping function has as input, an image patch corresponding to the current hypothesis parameters and as output the target parameter displacement. Each current hypothesis will yield a new hypothesis through the regression function which converges to the correct object parameters when learned successfully. The regressed hypotheses are passed through the incrementally increasing marginal spaces during both the training and objected detection in a new image. Possible advantages of MSDR relative to traditional discriminative learning are that MSDR heavily leverages context information, MSDR learns a smoother output function than a binary classifier which improves robustness, and MSDR is efficient by learning only in the projected subspaces (marginal search spaces). In addition, a regression function trained using a deep neural network can be iteratively applied to converge to the correct parameter region and eliminate outliers.

In MSDR, for a particular search space, the complex problem of learning a regression function from image data is solved by using a deep learning artificial neural network architecture that extracts directly from an image patch, the relevant features. According to an advantageous implementation, complex image patterns can be encoded in hierarchical features by learning one or more hidden layers by stacking deep neural network architectures, as described above. To solve the regression problem for a particular search space, at the output layer either a discretized multi-class classifier or a linear/non-linear regressor can be trained on top of the neural network features extracted by the learned hidden layers. Accordingly, such a deep neural network regression function has the ability to encode complex patterns hierarchically with no dependency on hand-crafted image features, and the ability to take advantage of unlabeled data to pre-train the underlying neural network (e.g., using stacked auto-encoder architectures or a deep-belief network). Such a trained deep neural network regressor also has the ability to solve multi-class problems. Object detection can be realized, for example, by hierarchical regression searches in an input image over the learned parameters spaces and taking the top hypotheses in the final parameter space. Object tracking can be accomplished similarly starting from the parameter set given by the object in a reference image.

Figure 3:
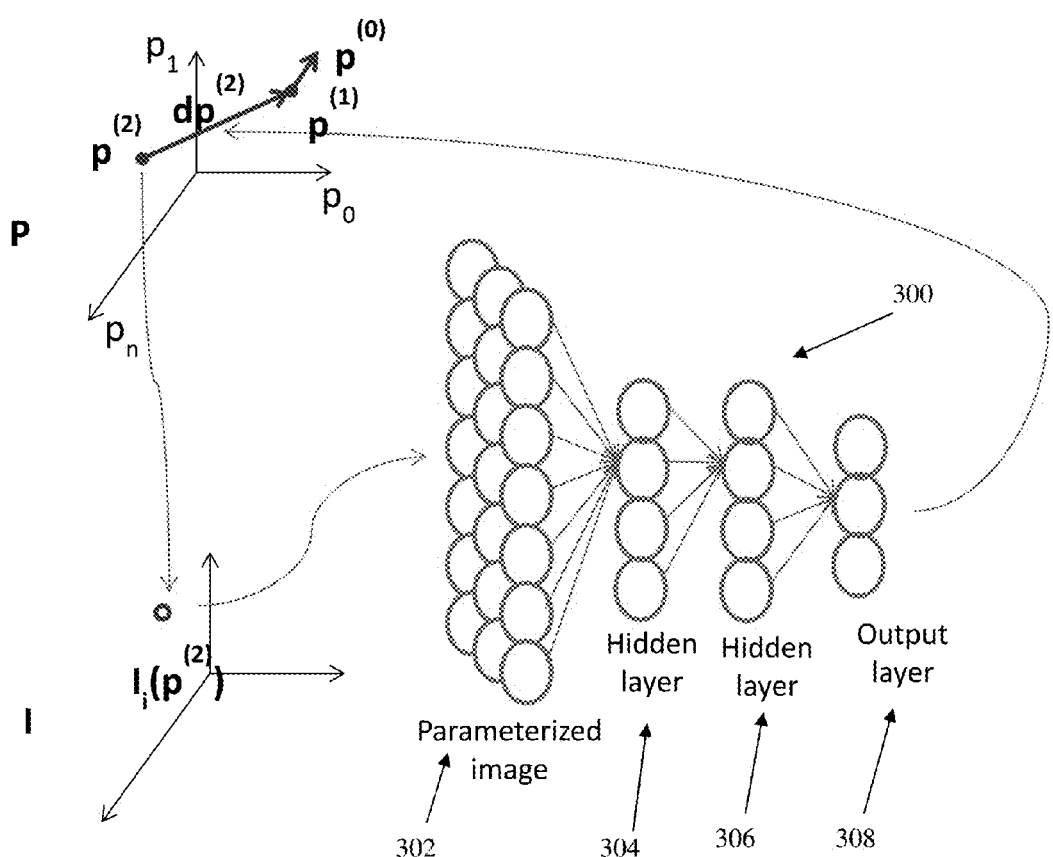
FIG. 3 illustrates training a deep multi-layer neural network regressor for a particular parameter space.

In order to train a deep neural network regressor (step 108 of FIG. 1), given a database of training images with the target object annotated in all or a subset of the training images, the object location (pose) is parameterized and the marginal spaces hierarchy is established, as described above in step 104. As described above in step 106, hypotheses are generated in the current search space. For the first search space, the hypotheses are generated directly from the current range, and for the other search spaces, the hypotheses are generated from the current hypotheses set augments with additional parameters which are sampled from the current corresponding range. Given the set of hypotheses for the current search space, a deep multi-layer neural network is trained having as input the sub-image (image patch) parameterized by the corresponding hypothesis parameters and as output the difference between the current parameters and the target or ground truth parameters of the target anatomical object for the current search space. FIG. 3 illustrates training a deep multi-layer neural network regressor for a particular parameter space. As shown in FIG. 3, P is the current parameter space (marginal space), $p^{(2)}$ is the parameters of a hypothesis in the parameter space, from which an image patch $I_i(p^{(2)})$ is generated from the $i^{th}$ image in the image space I. The parameterized image patch is used as input to a multi-layer deep neural network 300 and the supervised output is given by the parameter difference $dp^{(1)}$ between the hypothesis parameters $p^{(2)}$ and the ground truth parameters $p^{(1)}$ in the current parameter space P and optionally a confidence measure. The deep neural network 300 can be trained directly on the difference to the ground truth (in which case $p^{(1)}$ is the annotated parameter set) or the deep neural network 300 can be trained on a displacement towards ground truth in the training image. The deep neural network 300 has an input layer 302, multiple hidden layers 304 and 306, and an output layer 308. The input layer 302 directly inputs image patches corresponding to the parameters of hypotheses for the current parameter space. The hidden layers 304 and 306 can be trained to hierarchically extract features from the input image patches by stacking multiple deep neural network architectures in an unsupervised pre-training phase. The output layer 308 calculates displacement vector between the hypothesis parameters for each input image patch and the parameters of the target anatomical object for the current parameter space. An inverse of the distance of the estimated image patch to the ground truth image patch for the anatomical object location is used to train the confidence score.

For the deep neural network architecture and training, various types of neural networks can be used, such as convolutional neural networks (CNN), stacked restricted Boltzmann machine (RBM), or stacked auto-encoders (AE). In the case of RBM or AE, we can pre-train the networks in an unsupervised manner using all of the available training images (including non-annotated training images) to determine the representative features that characterize the class of data from a large database, prior to supervised training using the subset of annotated training images. In an advantageous embodiment, the deep neural network is trained using a stacked denoising auto-encoder (DAE) in two stages. The first stage is unsupervised where each layer of the multi-layer deep neural network is trained to reconstruct the input. In this stage, a virtual layer similar to the input is added to the output and the error to the input is minimized in this virtual layer to learn the weights for the nodes of each hidden layer. The second stage is supervised and the whole network error is minimized relative to the output training data starting from the pre-trained network weights. One characteristic of the DAE is that it randomly drops a certain percentage (up to 50%) of the inputs during training, which significantly increases the robustness of the resulting classifier or regressor. The output parameter space can be either directly regressed using a linear function or it can be discretized relative to the parameter range and solved as a multi-class classification problem. The second formulation has an advantage that it can directly encode the output probability and can generate multiple hypotheses, for example for different anatomical objects.

The set of current hypotheses for the current parameter space are then propagated through the trained deep neural network, and in a possible embodiment, the new set of hypotheses can be iteratively refined using the same deep neural network or through a newly trained deep neural network. This iterative process can eliminate samples far from the solution (non-overlapping) and generate samples closer to the true position to improve precision. FIG. 3 shows the results of this iterative process. As shown in FIG. 3, the image patch $I_i(p^{(2)})$ for the current hypothesis parameters $p^{(2)}$ is input to the deep neural network 300 in a first iteration, and the displacement vector $dp^{(2)}$ output by the deep neural network 300 maps the hypothesis parameters $p^{(2)}$ to the target parameters $p^{(1)}$. In a second iteration, the parameters $p^{(1)}$ are then input back into the deep neural network 300 in order to refine the estimated target parameters, and the deep neural network 330 outputs a displacement vector that maps the parameters $p^{(1)}$ to the refined target parameters $p^{(0)}$. Once the hypotheses for a particular marginal search space are run through the trained deep neural network, a new set of hypotheses is augmented with new parameters from the subsequent marginal space and the process is repeated for the subsequent marginal space. This results in a respective trained deep neural network regressor for each of the marginal spaces.

Figure 4:
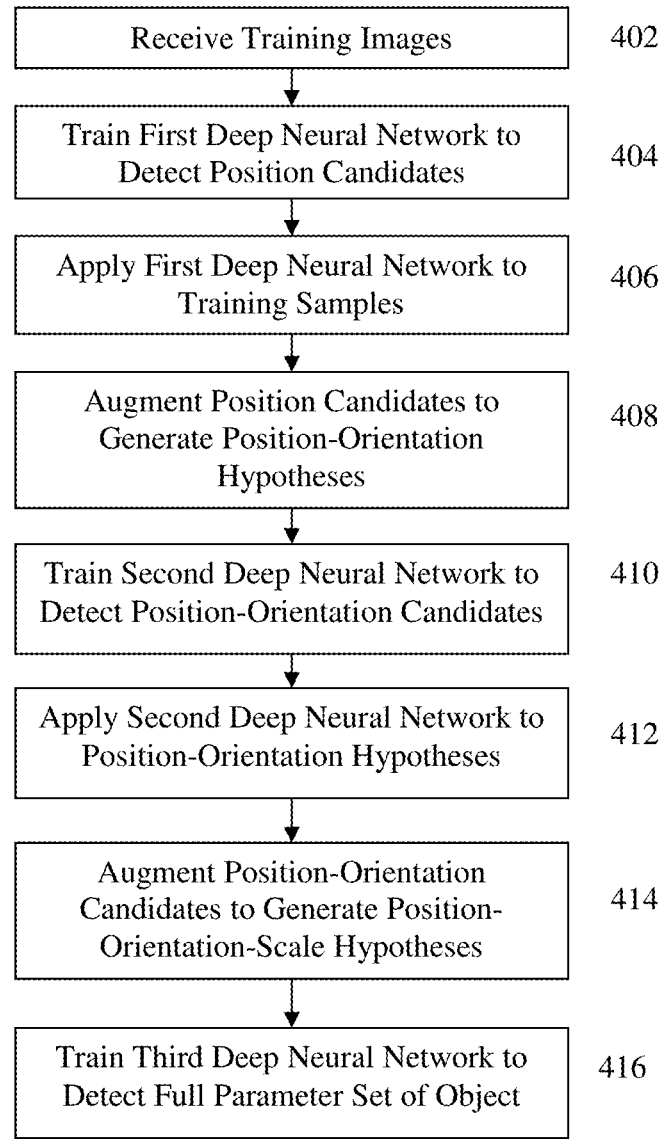
FIG. 4 illustrates training a series of deep neural networks in a series of marginal search spaces with increasing dimensionality according to an embodiment of the present invention.

FIG. 4 illustrates training a series of deep neural networks in a series of marginal search spaces with increasing dimensionality according to an embodiment of the present invention. In particular, the method of FIG. 4 provides a detailed method for training a series of deep neural networks for anatomical object detection in medical images when the parameter space of an anatomical object in a medical image is divided into marginal search spaces of position, position-orientation, and position-orientation-scale. Referring to FIG. 4, at step 402, training images are received. Step 402 of FIG. 4 can be implemented similarly to step 102 of FIG. 1. The training images can be 2D or 3D images, depending on the imaging modality and anatomical object to be detected. The description of FIG. 4 assumes that the images are 3D images and refers to the elements of the images as voxels. It is to be understood that the method of FIG. 4 can be similarly applied to 2D images and the term "pixel" can be substituted for "voxel" throughout the description of FIG. 4.

At step 404, a first deep neural network is trained to detect position candidates based on the training images. In a possible implementation, the first deep neural network may be a discriminative deep neural network that inputs voxels of an image as hypotheses and for each voxel calculates a probability that an image patch centered at the voxel is the object of interest. In this case, ground truth positions of anatomical objects in the training images can be used as positive training samples and randomly selected positions farther than a predetermined distance from the ground truth positions in the training images can be used as negative training samples. In another possible implementation, the first deep neural network may train a regressive function that inputs voxels of an image as hypotheses and calculates a difference vector for each input resulting in a predicted position calculated for each input voxel. In this case, a number of position hypotheses can be selected randomly from each training image, with the ground truth displacement to the position of the target anatomical object in the training image known for each position hypothesis. As described above, the first deep neural network (either discriminative or regressor) can be trained in two stages of unsupervised pre-training of the hidden layers (e.g., using stacked DAE) for learning complex features from input image patches and supervised training of the output layer based on the features extracted by the hidden layers and the annotated training samples.

At step 406, training samples are passed through the trained first deep neural network and a number of best position candidates are kept. For the discriminative deep neural network, a number of position hypotheses having the highest probability as calculated by the trained first deep neural network can be kept as the position candidates for each training image. For the deep neural network regressor, a confidence score can be calculated for each difference vector or each predicted position calculated by the trained first deep neural network, and a number of predicted positions with the highest confidence scores are kept as the position candidates At step 408, the position candidates are augmented with orientation parameters to generate hypotheses in the position-orientation search space. For example, a plurality of position-orientation hypotheses can be generated for each position candidate by rotating each image patch centered at a position candidate to a plurality of possible rotations. The range of these rotations can be determined by the range of orientations of the ground truth objects in the annotated training data.

At step 410, a second deep neural network is trained to detect position-orientation candidates based on the position-orientation hypotheses. In a possible implementation, the second deep neural network may be a discriminative deep neural network that inputs image patches of an image corresponding to the hypotheses in the position-orientation search space and for each image patch calculates a probability that the image patch is the object of interest. In another possible implementation, the second deep neural network may train a regressive function that inputs image patches of an image corresponding to the hypotheses in the position-orientation search space and calculates a difference vector in the position-orientation parameter space for each input resulting in a predicted position and orientation and a corresponding image patch in the image. The second deep neural network (either discriminative or regressor) can be trained in two stages of unsupervised pre-training of the hidden layers (e.g., using stacked DAE) for learning complex features from input image patches corresponding to the position-orientation hypotheses and supervised training of the output layer based on the features extracted by the hidden layers and the position-orientation hypotheses. Accordingly, the second deep neural network is trained based only on the position-orientation hypotheses that are generated from the position candidates detected using the first trained deep neural network.

At step 412, the position-orientation hypotheses are passed through the trained second deep neural network and a number of best position-orientation candidates are kept. For the discriminative deep neural network, a number of position-orientation hypotheses having the highest probability as calculated by the trained second deep neural network can be kept as the position-orientation candidates for each training image. For the deep neural network regressor, a number of image patches corresponding to the predicted positions and orientations with the highest confidence scores are kept as the position-orientation candidates.

At step 414, the position-orientation candidates are augmented with scale parameters to generate hypotheses in the position-orientation-scale search space. For example, a plurality of position-orientation-scale hypotheses can be generated for each position-orientation candidate by scaling each image patch corresponding to a position-orientation candidate to a plurality of possible scales. The range of these scales can be determined by the range of scales of the ground truth objects in the annotated training data.

At step 416, a third deep neural network is trained to detect a full parameter set (position-orientation-scale) of the object of interest based on the position-orientation-scale hypotheses. In a possible implementation, the third deep neural network may be a discriminative deep neural network that inputs image patches of an image corresponding to the hypotheses in the position-orientation-scale search space and for each image patch calculates a probability that the image patch is the object of interest. In another possible implementation, the third deep neural network may train a regressive function that inputs image patches of an image corresponding to the hypotheses in the position-orientation-scale search space and calculates a difference vector in the position-orientation-scale parameter space for each input resulting in a predicted position, orientation, and scale and a corresponding image patch in the image. The third deep neural network (either discriminative or regressor) can be trained in two stages of unsupervised pre-training of the hidden layers (e.g., using stacked DAE) for learning complex features from input image patches corresponding to the position-orientation-scale hypotheses and supervised training of the output layer based on the features extracted by the hidden layers and the position-orientation-scale hypotheses. Accordingly, the third deep neural network is trained based only on the position-orientation-scale hypotheses that are generated from the position-orientation candidates detected using the second trained deep neural network.

Figure 5:
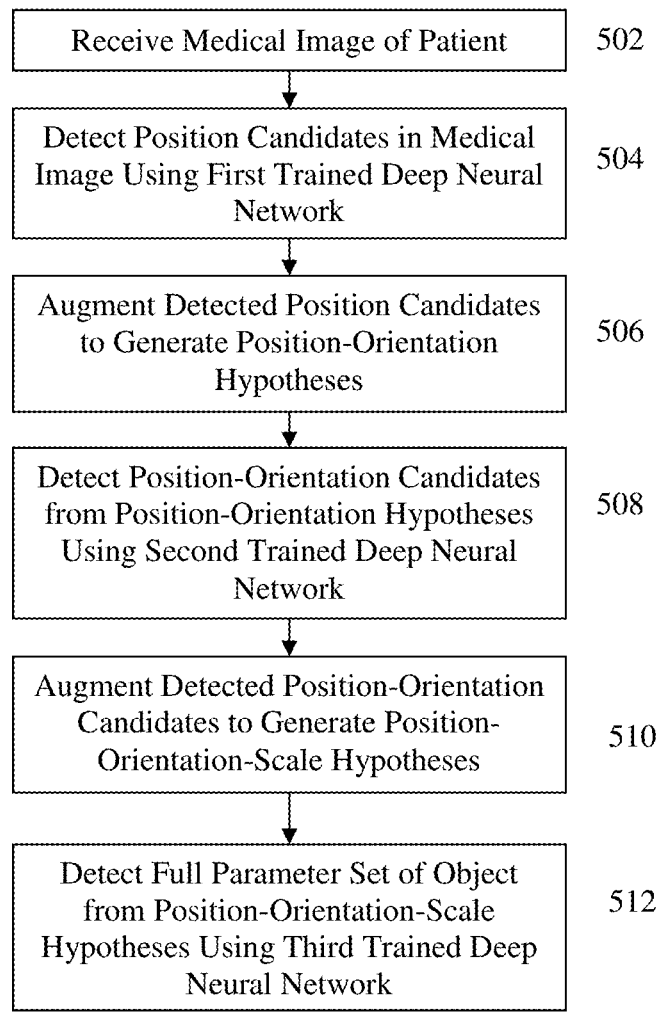
FIG. 5 illustrates a method of detecting an anatomical object in a medical image using a series of trained deep neural networks according to an embodiment of the present invention.

FIG. 5 illustrates a method of detecting an anatomical object in a medical image using a series of trained deep neural networks according to an embodiment of the present invention. The method of FIG. 5 can be performed using a series of deep neural networks trained using the method of FIG. 4. Referring to FIG. 5, at step 502, a medical image of the patient is received. The medical image can be 2D or 3D and can be acquired using any type of medical imaging modality, such as but not limited to CT, MRI, ultrasound, X-ray fluoroscopy, DynaCT, etc. The medical image can be received directly from an image acquisition device, such as a CT scanner, MRI scanner, etc., or can be received by loading a previously acquired medical image of the patient from a memory or storage of a computer system. The description of FIG. 5 assumes that the medical image is a 3D image and refers to the elements of the medical image as voxels. It is to be understood that the method of FIG. 5 can be similarly applied to 2D images and the term "pixel" can be substituted for "voxel" throughout the description of FIG. 5.

At step 504, position candidates are detected in the medical image using a first trained deep neural network. The first deep neural network operates directly on the voxels of the medical image, and not on handcrafted features extracted from the medical image. The first deep neural network inputs image patches centered at voxels of the medical image and calculates a number of position candidates in the medical image based on the input image patches. The first deep neural network can evaluate every voxel in the medical image or a subset of voxels in the medical image to calculate the position candidates. In a possible implementation, the first trained deep neural network may be a discriminative deep neural network that inputs image patches centered at voxels of the medical image and for each voxel calculates a probability that the voxel is the center position of the target anatomical object. In this case, a number of position candidates with highest probabilities calculated by the first trained deep neural network are kept. In another possible implementation, the first deep neural network may train a regressive function that inputs image patches centered at voxels of the medical image and calculates a difference vector for each voxel resulting in a predicted center position of the anatomical object calculated for each input voxel. In this case, the first trained deep neural network can also calculate a confidence score for each predicted position and a number of predicted positions with the highest confidence scores are kept.

At step 506, the position candidates detected by the first trained deep neural network are augmented with orientation parameters to generate position-orientation hypotheses. For example, a plurality of position-orientation hypotheses can be generated for each detected position candidate by rotating each image patch centered at a position candidate to a plurality of possible orientations sampled from a predetermined range of orientations for the target anatomical object. The predetermined range of orientations can be determined by the range of orientations of the ground truth objects in a set of annotated training data. It should be noted that in the case in which the second trained deep neural network used to detect position-orientation candidates in step 508 is a trained deep neural network regressor, the augmenting of the position candidates with orientation parameters may not be performed in some implementations. Although the additional position-orientation hypotheses may lead to increased accuracy of the position-orientation estimation, since the trained deep neural network regressor will predict the position and orientation of the target anatomical object and a corresponding target image patch for each input image patch corresponding to a position candidate, the trained deep neural network regressor can be run directly on image patches corresponding to the position candidates and it is not necessary to augment the position candidates with multiple orientation parameters.

At step 508, position-orientation candidates are detected from the position-orientation hypotheses using a second trained deep neural network. The second deep neural network operates directly on the image patches of the medical image corresponding to the position-orientation hypotheses. The second deep neural network inputs the image patches corresponding to the position-orientation hypotheses and calculates a number of position-orientation candidates in the medical image based on the input image patches. In a possible implementation, the second trained deep neural network may be a discriminative deep neural network that inputs the image patches corresponding to the position-orientation hypotheses and for each position-orientation hypothesis calculates a probability that the corresponding image patch is target anatomical object. In this case, a number of position-orientation candidates with highest probabilities calculated by the second trained deep neural network are kept. In another possible implementation, the second deep neural network may train a regressive function that inputs the image patches corresponding to the position-orientation candidates and calculates a difference vector for each image patch resulting in a predicted position and orientation of the anatomical object and corresponding predicted image patch calculated for each input position-orientation hypothesis. In this case, the second trained deep neural network can also calculate a confidence score for each predicted image patch and a number of predicted image patches with the highest confidence scores are kept as the position-orientation candidates.

At step 510, the position-orientation candidates detected by the second trained deep neural network are augmented with scale parameters to generate position-orientation-scale hypotheses. For example, a plurality of position-orientation-scale hypotheses can be generated for each detected position-orientation candidate by scaling each image patch corresponding to a position-orientation candidate to a plurality of possible scales sampled from a predetermined range of scales for the target anatomical object. The predetermined range of scales can be determined by the range of scales of the ground truth objects in a set of annotated training data. It should be noted that in the case in which the third trained deep neural network used to detect the full parameter set of the target anatomical object in step 508 is a trained deep neural network regressor, the augmenting of the position-orientation candidates with scale parameters may not be performed in some implementations. Although the additional position-orientation-scale hypotheses may lead to increased accuracy of the full parameter set estimation, since the trained deep neural network regressor will predict the position, orientation, and scale of the target anatomical object and a corresponding target image patch for each input image patch corresponding to a position-orientation candidate, the trained deep neural network regressor can be run directly on image patches corresponding to the position-orientation candidates and it is not necessary to augment the position-orientation candidates with multiple scale parameters.

At step 512, the full parameter set (position, orientation, and scale) of the target anatomical object is detected from the position-orientation-scale hypotheses using a third trained deep neural network. The third deep neural network operates directly on the image patches of the medical image corresponding to the position-orientation-scale hypotheses. The third deep neural network inputs the image patches corresponding to the position-orientation-scale hypotheses and calculates the full parameter set defining the pose of the anatomical object in the medical image based on the input image patches. In a possible implementation, the third trained deep neural network may be a discriminative deep neural network that inputs the image patches corresponding to the position-orientation-scale hypotheses and for each position-orientation-scale hypothesis calculates a probability that the corresponding image patch is the target anatomical object. In this case, the image patch corresponding to the position-orientation-scale hypothesis with the highest probability calculated by the third trained deep neural network can be output as the detection result for the anatomical object. It is also possible that a number of image patches corresponding to position-orientation-scale with the highest probabilities can be clustered to generate the final detection result for the anatomical object. In another possible implementation, the third deep neural network may train a regressive function that inputs the image patches corresponding to the position-orientation-scale hypotheses and calculates a difference vector for each image patch resulting in a predicted position, orientation, and scale of the anatomical object and corresponding predicted image patch calculated for each input position-orientation-scale hypothesis. In this case, the third trained deep neural network can also calculate a confidence score for each predicted image patch, and the image patch with the highest confidence score can then be output as the detection result for the anatomical object. It is also possible that a number of predicted image patches with the highest confidence scores can be clustered to generate the final detection result for the anatomical object.

The detected anatomical object can be displayed on a display device of a computer, for example, by displaying the medical image and indicating the pose of the target anatomical object on the medical image using a bounding box with the detected position, orientation, and scale. According to an advantageous embodiment, the method of FIG. 5 can be extended to segmentation of the of the target anatomical object. For example, a mean model (e.g., 3D mesh) of the target anatomical object can be calculated from a set of annotated training data, and once the full parameter (position, orientation, and scale) of the target anatomical object is detected in the medical image, the mean model can be rigidly registered to the medical image using the detected position, orientation, and scale of the target anatomical object, resulting in a segmented model of the target anatomical object in the medical image. In this case, local boundary refinement can be performed after the mean model is registered to the medical image. In the local boundary refinement, each boundary point of the segmented model of the target anatomical object is refined by evaluating points in both directions along a line normal to the model surface using the a trained boundary detector. The refined model can then be projected to a learned shape space of the target anatomical object using an active shape model. The steps of refining the model using the trained boundary detector and projecting the refined model to the learned shape space can be iterated until convergence or for a predetermined number of iterations. In a possible implementation, the trained boundary detector can be a deep neural network that is directly applied to the image data. Alternatively, the trained boundary detector can be use handcrafted features, such as steerable features, extracted from the image data.

The methods of FIGS. 4 and 5 describe training a series of deep neural networks and anatomical object detection using a trained series of deep neural networks for an embodiment in which the parameter space for the pose of an anatomical object is divided into the marginal search spaces of position, position-orientation, and position-orientation-scale. However, the present invention is not limited to these particular marginal shape spaces. For example, the methods can be similarly performed using marginal shape spaces of position, position-scale, and position-scale-orientation. It is to be understood, that embodiments of the present invention can be applied to any series of marginal search spaces with increasing dimensionality.

The methods of FIGS. 1 and 4 train a deep neural network for each of the marginal shape spaces. In one possible implementation, each of the trained deep neural networks is a discriminative deep neural network. In another possible implementation, each of the trained deep neural networks is a deep neural network regressor. Other hybrid implementations are also possible, where discriminative deep neural networks and deep neural network regressors are used for different ones of the marginal search spaces or where a deep neural network (discriminative or regressor) is used for one or more of the marginal search spaces and another type of classifier is trained for one or more of the marginal search spaces.

Figure 6:
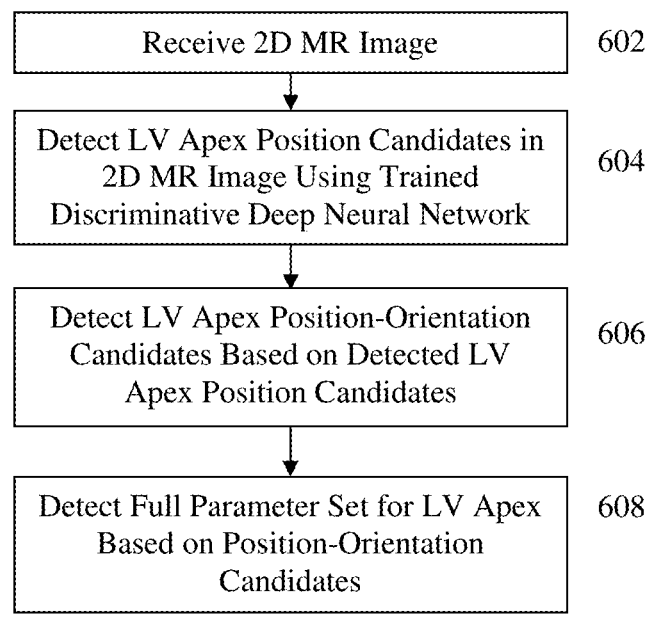
FIG. 6 illustrates a method for detecting a left ventricle apex in a 2D MR image using marginal space deep learning according to an embodiment of the present invention.

FIG. 6 illustrates a method for detecting a left ventricle apex in a 2D MR image using marginal space deep learning according to an embodiment of the present invention. The method of FIG. 6 provides an example in which deep neural networks are applied to detect the left ventricle (LV) apex in a 2D MR image. According to various possible implementations, the method of FIG. 6 can be implemented using discriminative deep neural networks for each marginal search space, using both a discriminative deep neural network and deep neural network regressors, or using a discriminative deep neural network with other types of classifiers. Although the method of FIG. 6 is described as detecting the LV apex in a 2D MR image, it is to be understood that variations of the method can be similarly applied to other anatomical objects and other 2D or 3D imaging modalities. Referring to FIG. 6, at step 602, a 2D MR image is received. The 2D MR image can be an MR image of a heart region of a patient. The 2D MR image can be received directly from an MR scanner or can be received by loading a previously acquired 2D MR image of a patient.

At step 604, LV apex position candidates are detected in the 2D MR image using a trained discriminative deep neural network. The trained discriminative deep neural network is trained based on training images in which the LV apex is annotated. For each training image, an image patch (e.g., 32×32 pixels) centered at the annotated LV apex can be taken as a positive training sample, and another image patch of the same size located more than a predetermined distance (e.g., 5 mm) away from the annotated LV apex can be randomly selected as a negative training sample. As described above, the discriminative deep neural network can be trained using an unsupervised pre-training stage in which the hidden layers are trained (e.g., using stacked DAE) to learn complex features from input image patches, followed by supervised training of the output layer based on the features extracted by the hidden layers and the annotated training samples to calculate a probability for each input image patch and classify an input image patch as positive or negative based on the probability.

In an exemplary test performed by the present inventors a training set of 7961 2D MR images from 184 patients was used. 75% of the training images were randomly selected for training (5970 images from 139 patients) and 25% for testing (1991 images from 46 patients). In this experiment, images from the same patient appear in either the training set or the testing set, but not both (patient-wise cross validation). For each training image, an image patch of 32×32 pixels centered at the annotated LV apex was selected as a positive training sample, and another image patch of the same size located more than 5 mm away from the annotated LV apex was be randomly selected as a negative training sample. With a balanced positive/negative training samples, a traditional MSL position classifier trained based on Haar wavelet features extracted from the training images using a probabilistic boosting tree (PBT) achieved a test error of 30% for LV apex position detection. The MSL position classifier can be trained on a very large number of negative samples. When the MSL position classifier was trained on 10 million negative training samples randomly selected from the training set, the test error of the MSL position classifier was reduced to 23%. A support vector machine (SVM) trained on the original input patch (using raw image intensity as features with 32×32=1024 features) achieved a test error of 13%. CNN achieved an error of 16.9%. A stacked DAE (SDAE) with layers having sizes of 1024-1024-300-100-2 trained based on the training samples achieved a test error of 7.3%, which is significantly better than the other classification schemes.

Figure 7:
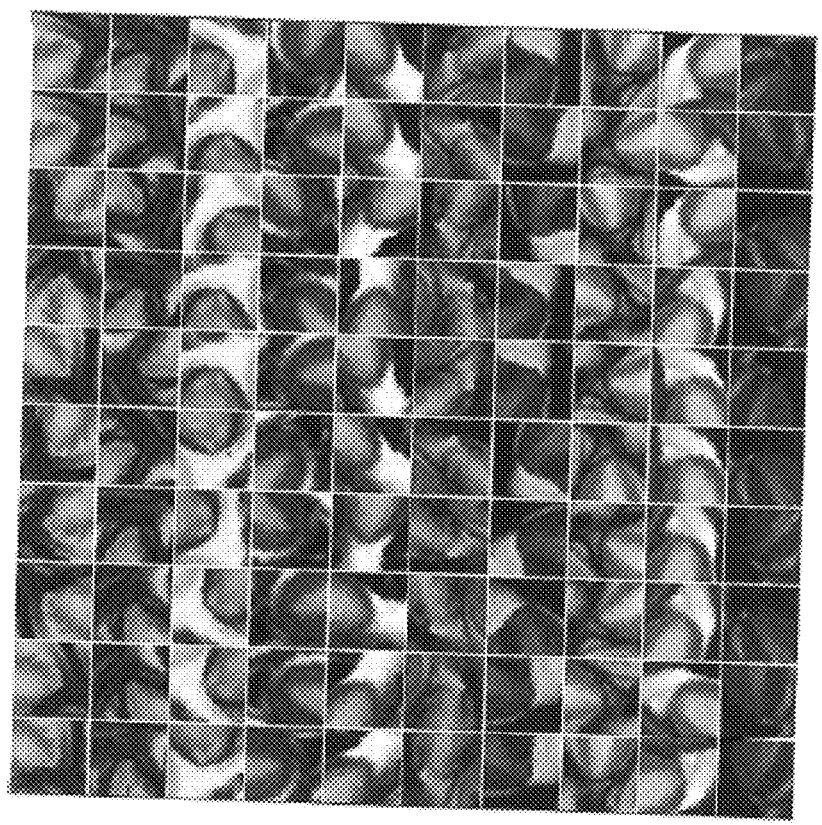
FIG. 7 illustrates exemplary enriched positive training samples with random rotations for LV apex position detection.
Figure 8:
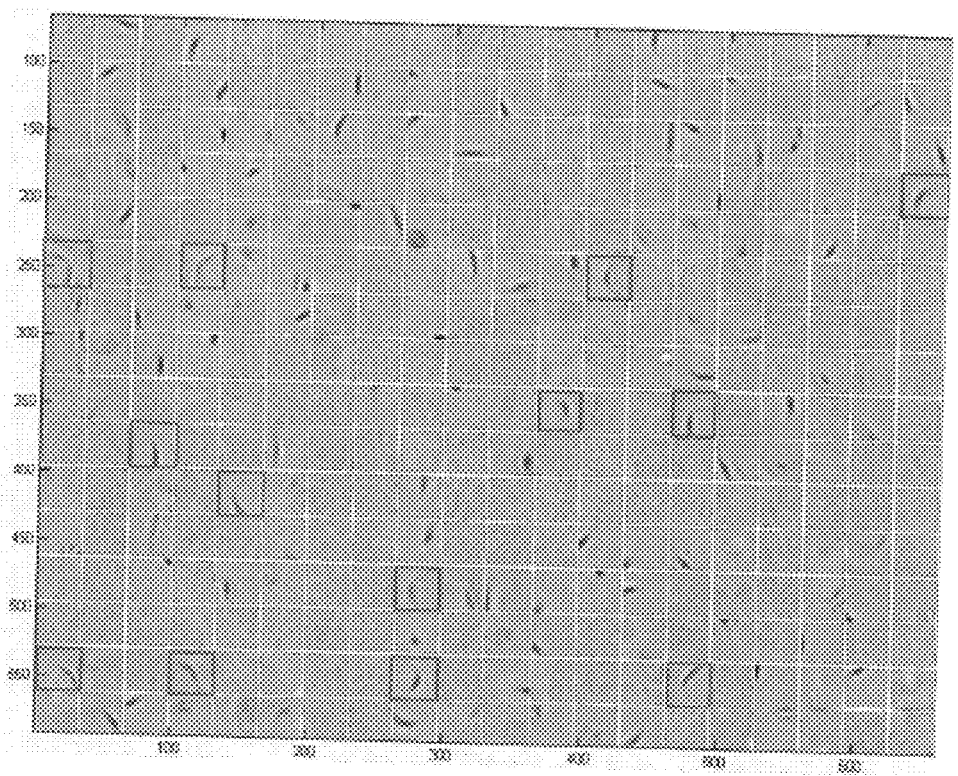
FIG. 8 illustrates exemplary learned weights of a first hidden layer of stacked denoising auto-encoder (DAE)

A major challenge with detection of the LV apex position in 2D MR images is that there is a large variation of the LV orientation, which leads to a large variation of the appearance of the LV apex based on the orientation of the MR image. According to an advantageous implementation, additional positive training samples for the LV apex detection can be generated by rotating each image patch centered at a ground truth LV apex position to a plurality of possible rotations. For example, for each training image, in addition to the original image patch centered at the annotated LV apex position, nine randomly rotated image patches centered at the annotated LV apex position can be used as positive training samples. FIG. 7 illustrates exemplary enriched positive training samples with random rotations for LV apex position detection. As shown in FIG. 7, each column shows 10 positive training samples taken from one training image. The top image patch in each column is the original image patch centered at the LV apex position for the training image, and the other image patches in each column are the randomly rotated image patches. The negative training samples are not rotated. However, since more positive training samples are selected from each training image, ten negative training samples can be randomly sampled from each training image in order to balance the number of positive and negative training samples. By training the SDAE for detecting the LV apex position using the enriched training samples in the experiment performed by the present inventors, the test error was reduced from 7.3% to 3.1%. As described above, the trained hidden layers of the deep neural network learn high-level image features directly from the input image patches. FIG. 8 illustrates exemplary learned weights of a first hidden layer of stacked denoising auto-encoder (DAE). The learned weights shown in FIG. 8 can be treated as filters for extracting high-level image features. Some of the filters (learned weights) shown in FIG. 8 are similar to Gabor features, while some of the filters (highlighted with boxes in FIG. 8) are specific detectors of the LV apex with different orientations.

Once the discriminative deep neural network position detector is trained, the trained discriminative deep neural network is used to test each pixel in the 2D medical image and a number (e.g., 200) of candidates with largest classification scores (highest probabilities) are preserved as position candidates. In a possible implementation, since the LV apex is an anatomical landmark, the method can end at this step and output a position detected by the trained discriminative deep neural network as the LV apex position. In this case, cluster analysis can be performed on the detected position candidates and the center of the largest cluster can be used as the final detection result for the LV apex. However, the position-orientation, and position-orientation scale detection can be used as bootstrapped classifiers to remove false positives in the position detection. In the testing performed by the present inventors, if a detected LV apex is more than 10 mm away from the ground truth, the detection is considered to fail. Using only the position detector trained with SDAE for LV apex detection achieved a failure rate of 16.3%. For comparison, using the whole MSL pipeline trained using handcrafted image features (Haar wavelets for position and steerable features for position-orientation and position-orientation-scale) and the PBT achieved a failure rate of 21.1%. Accordingly, the position detector trained with SDAE outperformed the entire MSL pipeline using handcrafted image features. In a possible hybrid approach, the position candidates for the LV apex can be detected using the SDAE, and the position candidates can be fed to the MSL position-orientation and position-orientation-scale classifiers trained using the handcrafted image features (steerable features) and the PBT. Using this hybrid approach, a detection failure of 11.7% was achieved, which is about half of the failure rate of the original MSL.

Returning to FIG. 6, at step 606, position-orientation candidates for the LV apex are detected based on the detected position candidates. In a first possible embodiment, the hybrid approach describe above can be used, in which the trained deep neural network replaces the position detector in the MSL pipeline and the detected position candidates are fed to the MSL position-orientation classifier trained using steerable features and a PBT. In other possible embodiments, deep neural network learning can be further applied to perform the position-orientation estimation.

In a second possible embodiment, similar to the method of FIG. 5 described above, rotated image patches centered at each of the position candidates can be cropped and input into a second trained discriminative deep neural network classifier which is trained as a binary classifier to distinguish an image patch corresponding to a correct hypothesis from an image patch corresponding to an incorrect hypothesis. A number of position-orientation candidates with the best classifications scores are preserved. This works well for 2D images since there is only one degree of freedom for 2D rotation, Furthermore, the 2D image can be pre-rotated to a number of possible orientations and the rotated image patches can be generated by cropping the image patches from the corresponding pre-rotated images. However, this may be impractical for 3D since there are three degrees of freedom for 3D rotation and rotating a 3D volume is time consuming.

In a third possible embodiment, steerable features can be used as image features to incorporate position and orientation hypotheses generated from the position candidates. The steerable features are efficient under any position, orientation and scale. In this embodiment, instead of using a PBT to train a classifier, a deep neural network can be used to train a discriminative classifier for detecting position-orientation candidates instead of the classifier based on the steerable features, and instead of training the classifier directly on the input image patches. The trained discriminative classifier is then used to detect the position-orientation candidates based on steerable features of position-orientation hypotheses generated from the detected position candidates.

In a fourth possible embodiment, the position-orientation problem is formulated as a regression problem and a trained deep neural network regressor is used to detect the position-orientation candidates based on the position candidates detected by the trained discriminative deep neural network. Given the input image patches corresponding to the position candidates, the trained deep neural network regressor can directly calculate estimates of the position and orientation of the target object (e.g., LV apex). Furthermore, the trained deep neural network regressor can be augmented to output a confidence score for each estimated target image patch. To train this confidence score, an inverse of the distance of the estimated image patch to the ground truth apex position is used. For each preserved position candidate, a corresponding image patch centered at the position candidate is input to the trained deep neural network regressor and a target image patch is predicted based on the input image patch. In this embodiment, the image patch corresponding to the position candidate does not need to be rotated. The trained deep neural network regressor provides not only an estimate of the target object position and orientation, but also a confidence score that quantifies how reliable the estimate is. The estimated position-orientation image patches are then ranked using the confidence score and a number of position-orientation candidates with the largest confidence scores are preserved.

At step 608, the full parameter set (position, orientation, and scale) is detected for the LV apex based on the position-orientation candidates. This step can be performed similarly to the position-orientation estimation step using one the embodiments described for that step. For example, in a first possible embodiment, the detected position-orientation candidates are fed to the MSL position-orientation-scale classifier trained using steerable features and a PBT. In a second possible embodiment, each of the image patches corresponding to the position-orientation candidates can be scaled to a plurality of scales and the scaled image patches can be evaluated by a trained discriminative deep neural network to detect the image patch with the highest classification score. In a third possible embodiment, a discriminative deep neural network trained using steerable features can be used to evaluate the position-orientation candidates at different scales. In a fourth possible embodiment, a trained deep neural network regressor can be used to estimate a target position-orientation-scale image patch for each of the position-orientation candidates, and the target image patch having the highest confidence score can be selected as the final detection result.

Figure 9:
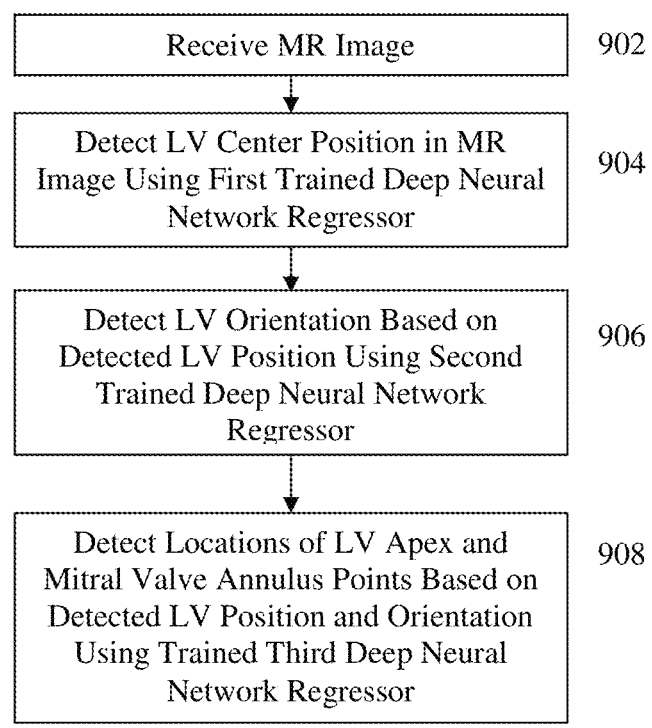
FIG. 9 illustrates a method for left ventricle (LV) landmark detection in MR cardiac long axis images using marginal space deep regression (MSDR) according to an embodiment of the present invention.
Figure 10:
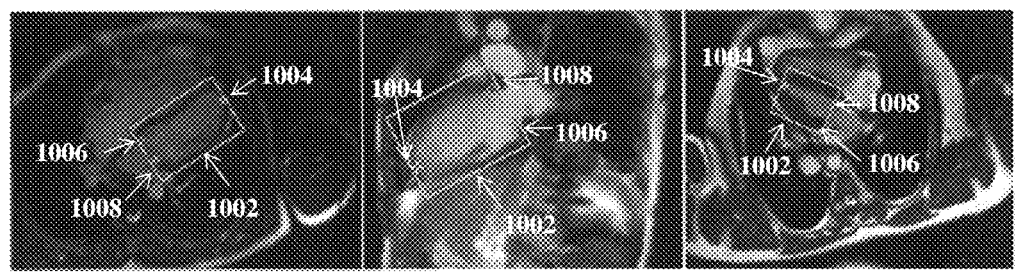
FIG. 10 illustrates exemplary LV landmarks in various MR cardiac long axis images.

FIG. 9 illustrates a method for left ventricle (LV) landmark detection in MR cardiac long axis images using marginal space deep regression (MSDR) according to an embodiment of the present invention. The method of FIG. 9 is an example in which a series of trained deep neural network regressors is used to detect multiple LV landmarks in a series of marginal spaces with increasing dimensionality. In particular, the method of FIG. 9 detects the locations of the LV apex and two mitral valve annulus points in MR cardiac long axis image. FIG. 10 illustrates exemplary LV landmarks in various MR cardiac long axis images. In particular, FIG. 10 shows an LV bounding box 1002 center at an LV center position, the LV apex 1004, and the mitral valve annulus points 1006 and 1008 in three MR long axis images. One difficulty with this detection problem is the large appearance and parameter variability characteristic to the MR images. All types of long axis views (e.g., 4-chamber view, 2-chamber view, and 3-chamber view) can be considered, which increases the difficulty of the problem.

Referring to FIG. 9, at step 902 an MR image is received. The MR image can be a 2D MR long axis image of any long axis view (e.g., 4-chamber view, 2-chamber view, or 3-chamber view). The MR image can be received directly from an MR scanner or received by loading a previously stored MR image from a memory or storage of a computer system. At step 904, an LV center position is detected in the MR image using a first trained deep neural network regressor. At step 906, an LV orientation is detected based on the detected LV position using a second trained deep neural network regressor. At step 908, locations of the LV apex and mitral valve annulus points are detected based on the detected LV position and orientation using a third trained deep neural network regressor. Instead of detecting a single anatomical object in a medical image in marginal search spaces of position, position-orientation, and position-orientation scale, the method of FIG. 9 performs the landmark detection in the following series of marginal search spaces: LV position, LV position and orientation, and a full parameter set including the positions of the LV apex and mitral valve annulus points. That is, the method of FIG. 9 finds the position and orientation of the LV (in steps 904 and 906) and then uses this information to predict the locations of the LV apex and mitral valve annulus points (in step 908).

The first trained deep neural network regressor using for LV position detection in step 904 is trained on 2D displacements from image patches (e.g., 32×32 pixels) corresponding to training sample position hypotheses to an image patch centered at the ground truth LV center position in each training image. The second trained deep neural network regressor is trained using predicted image patches output by the first trained classifier rotated to a number of different orientations to predict an image patch centered at the LV center position with the correct LV orientation. The third trained deep neural network regressor is trained on 2D displacements corresponding to locations of each of the three LV landmarks (LV apex and mitral valve annulus points). The third trained deep neural network regressor inputs an image patch corresponding to a detected LV center location and LV orientation and outputs a first displacement vector that maps the input image patch to a location of the LV apex, a second displacement vector that maps the input image patch to a location of one of the mitral valve annulus points, and a third displacement vector that maps the input image patch to the other one of the mitral valve annulus points. In an exemplary implementation, a 3-level DAE with a discretized multi-class output for each parameter value can be trained for each marginal search space. The trained DAEs may limit the length of the displacement vector (e.g., up to 24 pixel displacements for translation) and the image can be scanned iteratively to determine the final parameter set for each marginal search space.

Figure 11:
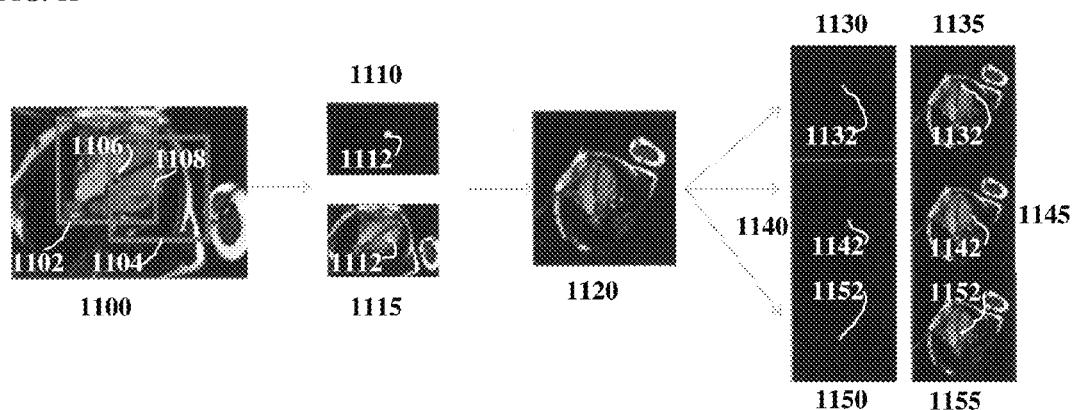
FIG. 11 illustrates exemplary results of detecting the LV landmarks in an MR image using the method of FIG. 9.

FIG. 11 illustrates exemplary results of detecting the LV landmarks in an MR image using the method of FIG. 9. As shown in FIG. 11, image 1100 shows a first detection stage (step 904 of FIG. 9), in which the LV position is detected using the first trained deep neural network regressor. As shown in image 1100, image patches 1102 and 1104 centered at various pixels in an MR image are input to the first trained deep neural network regressor, and the first trained deep neural network regressor calculates a respective displacement 1106 and 1108 for each image patch 1102 and 1104 from a center position of each image patch 1102 and 1104 to an LV center position. Image 1110 shows the detected LV center position 1112 detected by the first trained deep neural network regressor in the parameter space and image 1115 shows the detected LV center position 1112 in the MR image. As described herein, the first detection stage (step 904) detects a single LV center position. For example, the LV center position detected by the first trained deep neural network regressor with the highest confidence score can be propagated to the second detection stage (step 906). In an alternative implementation, multiple LV center position candidates can be propagated to the second detection stage. In the second detection stage (step 906), the LV orientation is detected based on the detected LV center position by the second trained deep neural network regressor. Image 1120 shows the MR image rotated to be aligned with the LV rotation detected by the second trained deep neural network regressor. As described herein, the first detection stage (step 904) predicts an image patch corresponding to a particular LV center position and LV orientation. In an alternative implementation, multiple LV position-orientation candidates can be propagated to the third detection stage. In the third detection stage (step 909), the positions of the LV apex and mitral valve annulus points are detected based on the detected LV center position and LV orientation by the third trained deep neural network regressor. Image 1130 shows the detected LV apex position 1132 detected by the third trained deep neural network regressor in the parameter space and image 1135 shows the detected LV apex position 1132 in the MR image. Image 1140 shows the detected position of the first mitral valve annulus point 1142 detected by the third trained deep neural network regressor in the parameter space and image 1145 shows the detected position of a first mitral valve annulus point 1142 in the MR image. Image 1150 shows the detected position of a second mitral valve annulus point 1152 detected by the third trained deep neural network regressor in the parameter space and image 1155 shows the detected position of the second mitral valve annulus point 1152 in the MR image.

Figure 12:
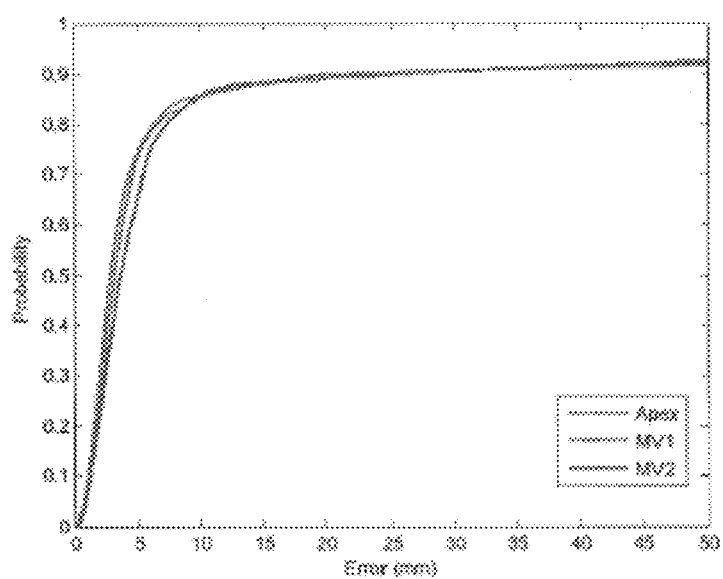
FIG. 12 illustrates the probability of detection errors on a testing set for the detection of LV apex and mitral valve annulus points.

The present inventors tested the method of FIG. 9 using a database of 7961 images from 184 patients, which was randomly split into 5970 images for training (75% of the data from 138 patients) and 1991 images for testing (25% of the data from 46 patients). The training and testing sets were disjoint at the patient level. For the first and second marginal search spaces, half of the original image was used with an image patch of 32×32 pixels. A 3-level DAE with discretized multi-class output for each parameter value was used for each marginal search space (up to 24 pixel displacements for translation). Each testing image was scanned iteratively to determine the final parameter set. FIG. 12 illustrates the probability of detection errors on the testing set for the detection of the LV apex and mitral valve annulus points. As shown in FIG. 12, 80% of the testing data has an error of less than 8 mm. Table 1 shows the performance of the method of FIG. 9 for detecting the LV center, LV apex, right mitral valve annulus point, and left mitral valve annulus point in the testing set without bootstrapping.

TABLE 1

| Anatomy | Mean | Median | 80$^{th}$ percentile | Failure rate (>10 mm) |
|---|---|---|---|---|
| LV center | 9.09 | 4.80 | 8.44 | 5.00 |
| LV apex | 12.28 | 3.61 | 6.26 | 14.37 |
| MV right | 12.05 | 3.16 | 6.80 | 14.32 |
| MV left | 11.00 | 2.85 | 6.53 | 14.63 |

For comparison, detection of the LV apex using the traditional MSL framework achieves a mean error of 20.39 mm, a median error of 4.38 mm, 11.04 mm at 80%, and 21.1% outliers (error larger than 10 mm from ground truth). Performance of the LV landmark detection using MSDR can be further improved by bootstrapping the results through the newly trained multi-layer neural networks to filter the hypotheses set. The detection time for the testing using the MSDR framework of FIG. 9 was less than 2 seconds using a standard personal computer (PC).

When a deep neural network architecture is used for the underlying classifier for object detection in a particular parameter space, as in the embodiments described above, scalability may be limited when searching in high dimensional spaces (such as search over the 3D position in a volume) due to scanning with high dimensional and complex weight matrices learned for such deep neural networks. This may apply for convolutional layers as well as fully connected filters, even though the operations of convolutional layers can be performed efficiently, for example by mapping the convolution through Fourier space using a Fast Fourier transform (FFT). According to an embodiment of the present invention, a method for approximating the marginal space deep neural network architectures can be used to address such scalability challenges.

Figure 13:
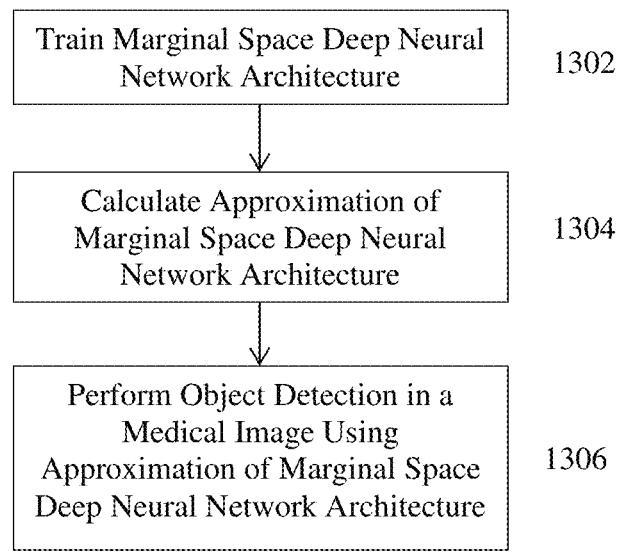
FIG. 13 illustrates a method of anatomical object detection by approximating a marginal space deep neural network architecture according to an embodiment of the present invention.

FIG. 13 illustrates a method of anatomical object detection by approximating a marginal space deep neural network architecture according to an embodiment of the present invention. The method of FIG. 13 can be applied to object detection using discriminative deep neural network architecture or a deep neural network regression function architecture. Referring to FIG. 13, at step 1302, a marginal space deep neural network architecture is trained for anatomical object detection. For example, the marginal space deep neural network architecture can be trained by training a series of deep neural networks for a series of marginal search spaces of increasing dimensionality using the method of FIG. 1 or the method of FIG. 4, described above. As described above, each deep neural network is trained by learning weights connecting nodes of multiple layers of the deep neural network. At step 1304, an approximation of the marginal space deep neural network architecture is calculated. The approximation of the marginal space deep neural network architecture is calculated by calculating a respective approximation of each trained deep neural network. The approximation of each trained deep neural network is calculated by approximating the learned weights of that trained deep neural network. At step 1306, the object detection in a medical image is performed using the approximation of the marginal space deep neural network architecture instead of the originally trained marginal space deep neural network architecture.

According to various possible embodiments, approximation of the weights for a trained deep neural network (step 1304) can be performed by: a) low rank tensor decompositions; b) approximation through more efficient features; or c) learning weights in separable low spaces directly using sparse approximated weight matrices. The goal of using approximated weight matrices is to maintain the classification performance of the already trained marginal space deep neural network architecture while significantly improving the speed of applying the marginal space deep neural network architecture over the input hypotheses. For example, using separable tensor decomposition in 3D, the computational complexity can be reduced for a volume of $n^3$ voxels filtered/convolved with a kernel $k^3$ voxels from the order of $(k^3 \cdot n^3)$ to the order of $(k \cdot n^3)$. In the context of anatomical object detection, the approximation of the weight matrices in the marginal space deep neural network architecture can be combined with a cascade classifier architecture trained on the already learned image features. The cascade can be trained using greedy incremental feature selection from the first network layer of features and then fine tuning the cascade for close to a 100% true positive rate.

According to a possible embodiment, given an already trained marginal space deep neural network architecture, trained weights can be approximated (step 1304) through low rank tensor factorization methods. It can be noted that in high dimensions, this task is in general NP-hard without guarantees for a globally optimal approximation solution. Accordingly, most low rank tensor factorization approaches are based on iterative optimization of a distance function between the target tensor and its low rank representation. Optimizations focus on either minimizing the two-norm (least squares) error under identically distributed noise or the Kullback-Leibler divergence between the low rank decomposition and the target tensor. Any such method for low rank tensor factorization can be used in order to approximate the learned weights of the trained deep neural networks. In advantageous implementation, the learned tensor weights of each trained deep neural network can be replaced with an approximating decomposition by fixing either the rank or the minimized error of the reconstruction. The approximation of a particular trained deep neural network can be refined iteratively by one of the following procedures: (1) After each full rank training epoch, project each of the tensors in the low rank space and repeat iteratively until the error remains stable; or (2) At each epoch, directly update the weights in the low rank space and repeat iteratively until the error remains stable.

Figure 14:
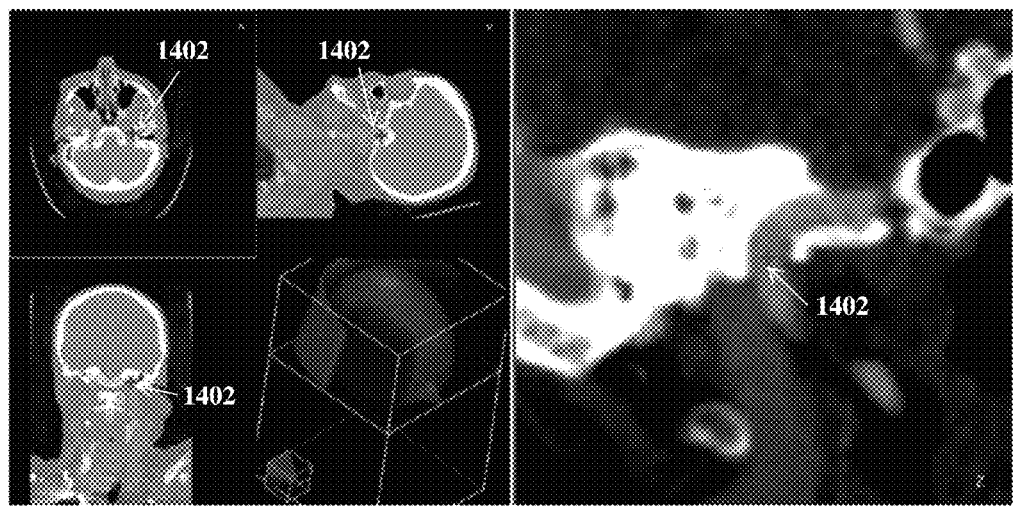
FIG. 14 illustrates exemplary results of landmark detection in a whole body computed tomography (CT) scan using an approximation of a trained marginal space deep neural network architecture.

FIG. 14 illustrates exemplary results of landmark detection in a whole body computed tomography (CT) scan using an approximation of a trained marginal space deep neural network architecture. As shown in FIG. 14, a target vascular landmark 1402 was detected in a whole body CT volume using an approximation of a trained marginal space deep neural network architecture. In the example of FIG. 14, a database of 272 annotated 3D CT volumes from 206 patients was used, with 204 volumes used for training and 68 volumes used for testing. The input box scanned over the image has a size of 20×20×20 mm. A discriminative marginal space deep neural network architecture with convolutional layers was trained with bootstrapping with the following architecture: 1: 6 convolutional layers with 5×5×5 kernels; 2: aggregation layer with 2×2×2 kernel; 3: 6×12 convolutional layers with 5×5×5 kernels; 4: aggregation layer with 2×2×2 kernel; 5: linear classifier layer with two classes. A rank 2 decomposition was used for approximating the weights of the marginal space deep neural network architecture. In this example, the full rank marginal space deep neural network architecture achieved a classifier error on the testing data of 2.0%. The full rank marginal space deep neural network architecture achieved training error with a mean of 1.38 mm, a standard deviation of 0.67 mm, a median of 1.25 mm, and an error at the $80^{th}$ percentile of 1.90 mm. The full rank marginal space deep neural network architecture achieved testing error with a mean of 1.49 mm, a standard deviation of 1.07 mm, a median of 1.32 mm, and an error at the $80^{th}$ percentile of 2.06 mm. The reduced rank approximation of the marginal space deep neural network architecture achieved an approximating classifier error on the testing data of 3.0%. The reduced rank approximation of the marginal space deep neural network architecture achieved training error with a mean of 1.34 mm, a standard deviation of 0.63 mm, a median of 1.28 mm, and an error at the $80^{th}$ percentile of 1.73 mm. The reduced rank approximation of the marginal space deep neural network architecture achieved testing error with a mean of 1.62 mm, a standard deviation of 1.36 mm, a median of 1.36 mm, and an error at the $80^{th}$ percentile of 2.09 mm. Accordingly, the performance of the approximation of the marginal space deep neural network architecture is very similar to that of the full rank marginal space deep neural network architecture. However, the run time of the reduced rank approximation is much faster than that of the full rank marginal space deep neural network architecture.

The use of deep neural network architectures for detection and segmentation of 3D objects in volumetric (3D) medical image data may require scanning large volumetric input spaces. This requires significant computational resources due to the large, high-dimensional input space and the complex weight matrices learned for such deep neural networks. This may apply for convolutional layers as well as fully connected filters. In an advantageous embodiment of the present invention, sparse adaptive deep neural networks (SADNN) (also referred to herein as sparse deep neural networks) are trained to learn representations of from 3D medical image modalities and are used in place of convolutional or fully connected deep neural networks to perform 3D object detection and segmentation in volumetric medical image data. The terms "sparse adaptive deep neural network (SADNN) and "sparse deep neural networks" are used herein interchangeably. Embodiments of the present invention train SADNNs by injecting sparsity into deep neural network architectures, which results in a considerable increase in computational efficiency while also providing regularization and reducing overfitting of the deep neural network architectures to the training data. Two alternative embodiments for injecting sparsity are described herein, one based on threshold enforcement, adjusted incrementally during the learning process, and another using a robust regularization scheme. In essence, these embodiments replace the uniform sampling pattern used for standard features with an adaptive, self-learned pattern. According to an advantageous embodiment of the present invention, SADNNs are integrated into the marginal space deep learning (MSDL) framework described above in connection with FIGS. 1,4, and 5. In particular, respective SADNNs can be trained for each of a plurality of marginal search spaces (e.g., position, position-orientation, and position-orientation-scale) and used to segment a 3D anatomical object in an input 3D medical image.

In each stage of MSDL, the detection of candidates in the respective marginal search space is essentially reduced to a patch-wise classification task described by a set of m parameterized input patches X (i.e., observations) with a corresponding set of class assignments y, specifying whether the target anatomical structure is contained in the patch or not. In a representation learning approach for training a deep neural network, such inputs are processed to higher-level data representations using the inter-neural connections, defined as kernels under non-linear mappings. For general notation purposes, the parameters of a convolution filter for a given neuron (node) in the network can be defined as the pair (w,b), where w encodes the weights and b represents the associated bias. The same notation holds for a fully connected layer, which can conceptually be regarded as a convolution layer with the filter size equal to the underlying feature-map size. From the perspective of a given neuron in a fully connected layer, this means that the neuron is connected to all the neurons in the previous layer and a corresponding weight is learned for each connection. A fully connected deep neural network can be defined with the parameters (w,b), where $w=(w_1, w_2, \ldots w_n)^T$ represents the parameters of all n concatenated kernels over the layers of the network, i.e., the weighted connections between neurons, and b encodes the biases of the neurons. In this case of the fully connected deep neural network, n also represents the number of neurons in the network, as there is a one-to-one association between neuron and kernel. In order to compute the response or so-called activation of a given neuron, a linear combination is computed between the weights of all incoming connections and the activations of all neurons from where the incoming connections originate. The bias of this neuron is then added to this linear combination, and the resulting value is transformed by a non-linear mapping to obtain the activation value. In mathematical terms, from the perspective of the k-th neuron in the network, its activation value $o_k$ is given by:

$$o_k = \delta(x_k^T w_k + b_k), \quad (1)$$

where $\delta$ represents a non-linear activation function, $w_k$ denotes the weights of incoming connections, $x_k$ denotes the activations of the connected neurons from the previous layer, and $b_k$ denotes the bias of the neuron. If the neuron is part of the first layer, $x_k$ is given by the voxel values of the input image patch.

Regarding the activation function δ used to synthesize the input information, different functions can be used for different learning problems. For example, possible functions include the identity function, rectified linear units (ReLU), the hyperbolic tangent, or the sigmoid function. In an advantageous implementation, the sigmoid function defined as $δ(y)=1/(1+e^{-Y})$ is used as the activation function, in order to build through the deep neural network a multivariate logistic regression model for classification.

In training a deep neural network for a particular parameter space, the network response function, defined as $\mathcal{R}(\bullet; w;b)$, can be used to approximate the probability density function over the class of labels, given an input sample:

$$\mathcal{R}(x^{(i)};w;b) \approx p(y^{(i)}|x^{(i)};w;b), 1 \leq i \leq m. \quad (2)$$

Given the supervised setup and considering the independence of the input observations, the Maximum Likelihood Estimation (MLE) method can be used to learn the network parameters in order to maximize the likelihood function:

$$(\hat{w},\hat{b}) = \underset{w,b}{\operatorname{argmax}} \mathcal{L}(w, b, X) = \underset{w,b}{\operatorname{argmax}} \prod_1^m p(y^{(i)} | x^{(i)}; w; b), \quad (3)$$

where m represents the number of training samples. In other words, the network parameters are estimated such that for every training sample $x^{(i)}$, the network predicts with high confidence its true class label $y^{(i)}$ ($1 \leq i \leq m$). This is equivalent to minimizing a cost function $C(\bullet)$ quantifying how well the network prediction matches the expected output, i.e., the true label. The $L_2$ penalty function is used to reduce the maximization problem expressed in Equation (3) to the following minimization problem:

$$(\hat{w},\hat{b}) = \underset{w,b}{\operatorname{argmin}}[C(X, w, b) = \|\mathcal{R}(X; w; b) - y\|_2]. \quad (4)$$

This minimization problem is solved using the Stochastic Gradient Descent (SGD) method. Using a random set of samples $\tilde{X}$ from the training data, a feed-forward propagation is performed to compute the network response $\mathcal{R}(\tilde{X}; w;b)$. Denoting the network parameters in the t-th optimization step as $w(t)$ and $b(t)$, they are updated according to the following rules:

$$w(t+1) = w(t) - η \nabla_w C(\tilde{X};w(t);b(t))$$

$$b(t+1) = b(t) - η \nabla_b C(\tilde{X};w(t);b(t)), \quad (5)$$

where ∇ denotes the gradient of the cost function with respect to the network parameters and η denotes the magnitude of the update, i.e., the learning rate. The backpropagation algorithm is used to compute the gradients. The backpropagation algorithm computes $\nabla_w C(\tilde{X};w(t);b(t))$ and $\nabla_b C(\tilde{X};w(t);b(t))$ layer by layer from the last layer in the deep neural network to the first layer. $\tilde{X}$ is referred to as one batch of samples. One complete batch-wise iteration over the entire training data with a parameter update at each step is considered one training epoch. To train a powerful deep neural network based on this approach, a large number of epochs (e.g., 300) may be required.

Using deep neural networks trained as described above for object localization and boundary delineation in 3D context is computationally intensive and may be infeasible when the parameterized input samples become very large, such as in the cases of 3D bounding boxes enclosing large anatomical objects. Embodiments of the present invention address these challenges by providing layer sparsification in the training stage to generate a trained SADNN. Two alternative embodiments for injecting sparsity are described herein, one based on threshold enforcement, adjusted incrementally during the learning process, and another using a robust regularization scheme.

In one embodiment, threshold enforced sparsity is used to inject sparsity into deep neural network in order to train a SADNN. Threshold enforced sparsity injects sparsity into one or more layers of a deep neural network, such as a convolutional neural network (CNN) of fully connected deep neural network, by using a greedy approach to gradually eliminate low magnitude network connections during the training process. By removing weights with small absolute values, the affected neurons are able to recover and preserve their output response unchanged and also more invariant and robust. The sparsity increase occurs in iterative stages. In an initial or pre-training stage, the deep neural network is initially trained to learn the full set of weights. Then, at each subsequent iterative stage a number of weights with small magnitudes are set to zero, which has the effect of removing the weights and therefore the corresponding network connections from the deep neural network. The impact of this sparsity injecting procedure can be quantified with the parameter p ($0 < p < 1$), which represents the proportion of weights to be removed in a given iteration. At each stage, for each filter of a considered layer, a proportion of the remaining weights (defined by the value p) is set to zero. If $N_i$ represents the number of preserved (non-zero weights before the i-th stage, then $N_{i+1}=(1-p)N_i$. As such, in the i-th stage, the $pN_i$ weights having the smallest absolute value are eliminated (set to zero). Once these weights are eliminated in each stage, the deep neural network is re-trained for a small number of epochs (e.g., 10-20) using only the remaining weights. This allows the neurons to recover from the information loss, and adapt their response by learning new weights for the remaining incoming connections. To further sustain this recovery, the $L_1$ norm $\|w\|_1$ can be preserved over each injection stage by imposing a re-normalization in order to approximate the original response of the fully trained deep neural network. In an advantageous implementation, the process is finished when a target sparsity degree (e.g., 95%) is reached. In other words, the training is completed when the fraction $(1-p)^s$, specifying the remaining proportion of coefficients after s stages, reaches the preset target value. In another possible implementation, the training can be completed after a preset number of training stages or iterations are performed. The threshold enforced sparsity method may be applied only to the first hidden layer of the deep neural network, to all the hidden layers of the deep neural network, or to some other subset of hidden layers of the deep neural network.

The threshold enforced sparsity method permanently eliminates filter weights, while re-learning the remaining weights to provide the best possible approximation of the original filter response. Viewing the system deep neural network as a whole, the threshold enforced sparsity method aims to find a sparsity map s for the network weights w, such that over T training rounds, the response residual ε given by:

$$\epsilon = \|\mathcal{R}(X;w;b) - \mathcal{R}(X;w_s;b_s)\| \quad (6)$$

is minimal, where $b_s$ denotes the biases of in the sparse deep neural network and $w_s$ denotes the learned sparse weights, determined by the sparsity map s with $s_i \in \{0,1\}$, $\forall i$. FIG. 15 illustrates an algorithm for training a sparse adaptive deep neural network (SADNN) using iterative threshold enforced sparsity according to an embodiment of the present invention.

As shown in FIG. 15, at 1502, a deep neural network is pre-trained using all of the weights for a small number of epochs (e.g., 10-20). The pre-training stage induces a certain degree of structure in the filters, prior to eliminating coefficients. At 1504, the sparsity map s is initialized with all ones, representing that all of the weights remain at after the pre-training stage. The sparsity injection method of FIG. 15 is applied over a preset number of T training rounds (stages). In each round, at 1506, from the active weights of the considered filters, a percentage of active weights having the smallest absolute values are greedily selected and set to zero to permanently remove the corresponding neural connections from the deep neural network. The considered filters are the filters corresponding to the neurons of one or more hidden layers of the deep neural network to which sparsity is being injected. The sparsity map is updated to change the sparsity map values corresponding to the smallest active weights from one to zero, and set of weights is updated by multiplying individual weights by the corresponding sparsity map values to set the smallest active weights to zero. At 1508, a normalization is performed to preserve the $L_1$ norm of the remaining active weights of each filter from the previous training round. This approximates the original response for any given filter i by preserving its $L_1$ over all the training rounds. At 1510, the biases from the previous training round are kept. At 1512, in the final step of each iteration (training round) the supervised training of the deep neural network is continued on the remaining active connections, guiding the recovery of the neurons from the missing information by minimizing the original network loss function:

$$\left(\hat{w}^{(t)}, \hat{b}^{(t)}\right) = \underset{w:w^{(t)}, b:b^{(t)}}{\operatorname{argmin}} C(X, w, b), \quad (7)$$

where $w^{(t)}$ and $b^{(t)}$ (computed from the values in round t−1) are used as initialization for the deep neural network parameters in the optimization. This re-training of the deep neural network using only the remaining active connections results in adjusted values $\hat{w}^{(t)}$ and $\hat{b}^{(t)}$ for the remaining weights and the biases of the filters. The deep neural network can be trained for a small number of epochs (e.g., 10-20) in each training round. At 1540, the weights and biases after the final training round are used as the learned sparse weights and biases defining the SADNN.

The method of FIG. 15 learns highly sparse features with adaptive structure. When applied to the first hidden layer of a deep neural network, adaptive sparse data patterns are learned which capture the essential structures in the medical image data, explicitly discarding input voxels with minimal impact on the network response function $\mathcal{R}$. In an advantageous implementation, the parameter p, which represents the proportion of weights to be set to zero in a given iteration, can decrease with the number of training rounds, such that in later stages of the training, exponentially less filter weights are set to zero. The resulting adaptive sparse patterns from the iterative threshold enforced sparsity overcome the limitations of manually predefined sampling patterns used in handcrafted features, eliminating the need for feature engineering. In the experiments performed by the present inventors, the computed sparse patterns reach sparsity levels of 90-95%, meaning that only 5-10% of the weights of the low-level fully connected kernels can approximate the original deep neural network response $\mathcal{R}$. Furthermore, the spare network trained using the iterative threshold enforced sparsity even outperforms the original trained deep neural network since the sparsity acts as regularization and reduces the likelihood of overfitting during training.

In another embodiment, sparsity is induced in feature kernels of a deep neural network architecture by using a norm-enforcing regularization. In particular, in and advantageous implementation, an approximating penalty term called re-weighted $L_1$ norm (RL1) is used to drive a large number of filter weights to zero. The re-weighted $L_1$ norm penalty term overcomes computational limitations of the $L_0$ norm, while stile maintaining its advantages with respect to the underlying sparse penalization scheme. An adapted cost function including the re-weighted $L_1$ norm penalty term is given by:

$$C(w) = C_0(w) + \Sigma_i^N \lambda_i \|w\|, \quad (8)$$

where $C_0(w)$ is the initial cost function for the deep neural network, $\lambda = (\lambda_1, \lambda_2, \ldots \lambda_N)$ are re-weighting coefficients, and N denotes the total number of weights of all of the filters of the deep neural for which sparsity is being injected. For example, the re-weighted $L_1$ norm regularization can be applied to all of the filters of all layers of the deep neural network, to filters corresponding to neurons in only the first hidden layer of the deep neural network, or to some other subset of filters or layers of the deep neural network.

Figures 16, 17:
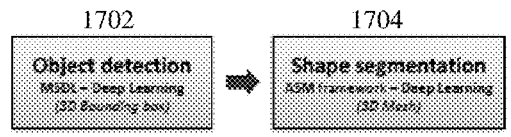
FIG. 16 illustrates an algorithm for injecting sparsity into a deep neural network using iterative re-weighted $L_1$ norm regularization according to an embodiment of the present invention.
FIG. 17 illustrates a schematic overview of a pipeline for segmenting a 3D anatomical object in a 3D medical image according to an embodiment of the present invention.

FIG. 16 illustrates an algorithm for injecting sparsity into a deep neural network using iterative re-weighted $L_1$ norm regularization according to an embodiment of the present invention. As illustrated in FIG. 16, at 1602, the iteration count l is set to zero, the re-weighting coefficients are initialized to one for all weights of all of the filters. At 1604, the weights $w^{(l)}$ of are estimated using a gradient backpropagation step based on the adapted cost function expressed in Equation (8). At 1506, the coefficients of the regularization term are updated based on the current weights. In particular, the updated re-weighting coefficients are calculated as $$\lambda_i^{(l+1)} = \frac{1}{\|w_i^{(l)}\| + \epsilon},$$

where $\epsilon$ is a constant with a small value (e.g., $\epsilon=0.1$) that is greater than zero. Steps 1604 and 1606 are then repeated until convergence of the weights or until a preset number of iterations are performed. This re-weighting scheme reduces the effect of the $L_1$ norm in the adapted objective function by multiplying each weight in the $L_1$ norm with a term approximating the inverse of its magnitude. The re-weighting of the $L_1$ norm makes the regularization look more like $L_0$ norm regularization, and drives a large number of weights that are less relevant to the final classification result to zero. The re-weighted $L_1$ norm regularization method of FIG. 16 can be implemented as a initial training stage in the training of a SADNN. Pre-training the deep neural network using this norm-enforcing regularization scheme forces the magnitude of a number of weights to drop to zero, thus removing those weights and the corresponding incoming connections from filters in the deep neural network, leading to a sparse deep neural network. After this stage, a threshold can be enforced, specifying the absolute limit for weight magnitudes, under which the connections are explicitly removed by setting the weights to zero. Then, the deep neural network is trained until saturation on the remaining weights, resulting in a trained SADNN.

The two methods described above for training sparse neural networks emulate in practice the benefits of regularization. By simplifying the deep neural network through parameter elimination, individual neurons are forced to learn more robust and effective representations. The neurons of the sparse neural networks become more insensitive to noise and other factors in the input image data that do not describe the underlying observations. In addition, the methods for training sparse neural networks described herein prohibit complex neural co-adaptions, reducing the risk of the sparse deep neural network overfitting the underlying training set. Furthermore, the sparse deep neural networks considerably boost evaluation speed, which is important when scanning large parameter spaces.

FIG. 17 illustrates a schematic overview of a pipeline for segmenting a 3D anatomical object in a 3D medical image according to an embodiment of the present invention. As shown in FIG. 17, the segmentation of a 3D anatomical object is performed in two stages: an object detection stage 1702 and a shape segmentation stage 1704. The object detection stage 1702 uses MSDL to detect a nine dimensional full similarity transformation in a series of marginal search spaces, resulting in a bounding box defining a pose (i.e., position, orientation, and scale) of the 3D anatomical object in the 3D medical image. The 3D pose of the object is used to align a mean 3D mesh of the object learned from training data with the 3D medical image, and the shape segmentation stage 1704 uses an active shape model (ASM) framework and a deep neural network classifier to calculate a non-rigid shape deformation to refine a boundary of the 3D mesh in the 3D medical image.

Figure 18:
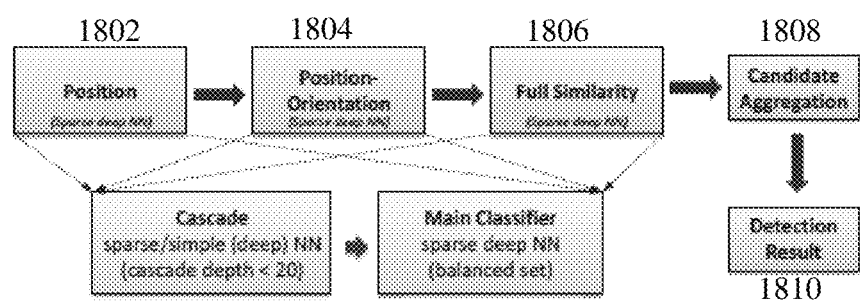
FIG. 18 illustrates a framework for marginal space deep learning (MSDL) using sparse deep neural networks according to an embodiment of the present invention.

In the embodiments of FIGS. 1, 4, and 5, described above, in order to detect a pose (bounding box) of an object in a 3D medical image using MSDL, a respective deep neural network can be trained for each of the series of marginal search spaces (e.g., position, position-orientation, and position-orientation-scale). In an advantageous embodiment of the present invention, the MSDL framework can utilize sparse deep neural networks such that respective sparse deep neural networks are trained for each marginal search space in the series of marginal search spaces. FIG. 18 illustrates a framework for marginal space deep learning (MSDL) using sparse deep neural networks according to an embodiment of the present invention. As shown in FIG. 18, a respective sparse deep neural network is trained for each of the position detection stage 1802, which detects object candidates in the position search space, the position-orientation detection stage 1804, which detects object candidates in the position-orientation search space, and the full similarity transformation detection stage 1806, which detects object candidates in the full similarity transformation parameter space. Once the full similarity transformation object candidates are detected, candidate aggregation 1808 is performed and the detection result 1810 is output. As shown in FIG. 18, the respective sparse deep neural network classifier for each of the position detection stage 1802, the position-orientation stage 1804, and the full similarity transformation stage 1806, includes a cascade and a main classifier. The main classifier is a sparse deep neural network trained with iterative threshold enforced sparsity or with re-weighted $L_1$ norm regularization, as described above. The cascaded is a series of simple, shallow (i.e., one hidden layer) sparse neural networks trained to eliminate a large number of negative training samples to provide a balanced sample set to the main sparse deep neural network classifier. The main sparse deep neural network classifier (in each marginal search space) is trained using the balanced set of training samples output by the cascade.

Figures 19, 20:
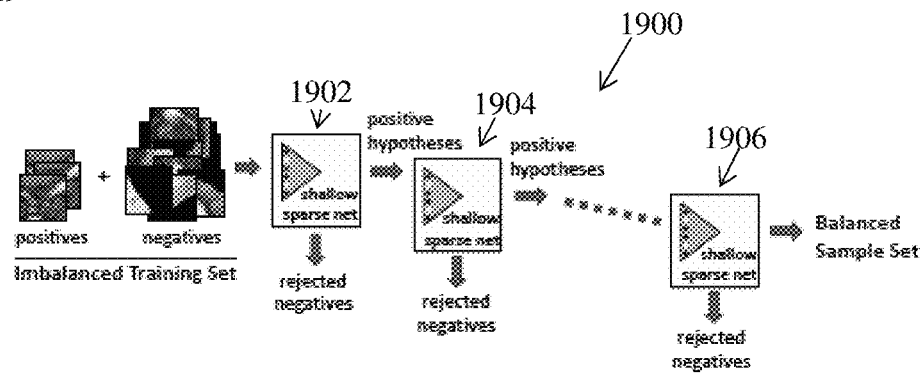
FIG. 19 illustrates a negative filtering cascade used to balance a training set according to an embodiment of the present invention.
FIG. 20 illustrates an algorithm for training a negative filtering cascade according to an embodiment of the present invention.

A challenge arising with the use of deep neural networks as the discriminating engine in each stage of the marginal space pipeline is the high class imbalance. This imbalance can reach ratios of 1:1000 positive to negative samples, impacting both the training efficiency and stochastic sampling of the gradient during learning, resulting in a bias of the classifier towards the overrepresented negative class. A deep neural network architecture cannot be trained with an SGD approach on such an unbalanced set, and simply re-weighting the penalties for the network cost function further worsens the vanishing gradient effect. According to an advantageous embodiment of the present invention, a negative filtering cascade of shallow (i.e., one hidden layer) neural networks to filter negative responses. FIG. 19 illustrates a negative filtering cascade used to balance a training set according to an embodiment of the present invention. As shown in FIG. 19, in each stage (1902, 1904, and 1906) of the cascade 1900, a shallow, sparse neural network is trained and its decision boundary is adaptively tuned to eliminate as many true negative hypotheses from the training set as possible. The remaining hypotheses, classified as positives, are propagated to the next stage of the cascade where the same filtering procedure is repeated unless a balanced sample set is achieved. In order to train a network within the cascade, we iterate at epoch level over the complete positive training set, while at each batch level, we randomly sample the negative training space to obtain a balanced training batch.

FIG. 20 illustrates an algorithm for training a negative filtering cascade according to an embodiment of the present invention. As illustrated in FIG. 20, at 2002, a shallow sparse neural network is trained. In an advantageous implementation, the shallow sparse neural network is a single hidden layer neural network that is trained using iterative threshold enforced sparsity or re-weighted $L_1$ norm regularization to inject sparsity into the single hidden layer. At 2004, the decision boundary d is set as the largest value for which the false negative rate (FNR) is zero. At 2006, the trained shallow sparse neural network is used to filter the negative samples based on the decision boundary. In particular, the trained shallow sparse neural network calculates a classification score for each sample, the classification score for each sample is compared to the decision boundary, and samples with classification scores lower than the decision boundary are rejected. Since the decision boundary is set so that the FNR=0, all of the rejected samples are true negative samples.

Figure 21:
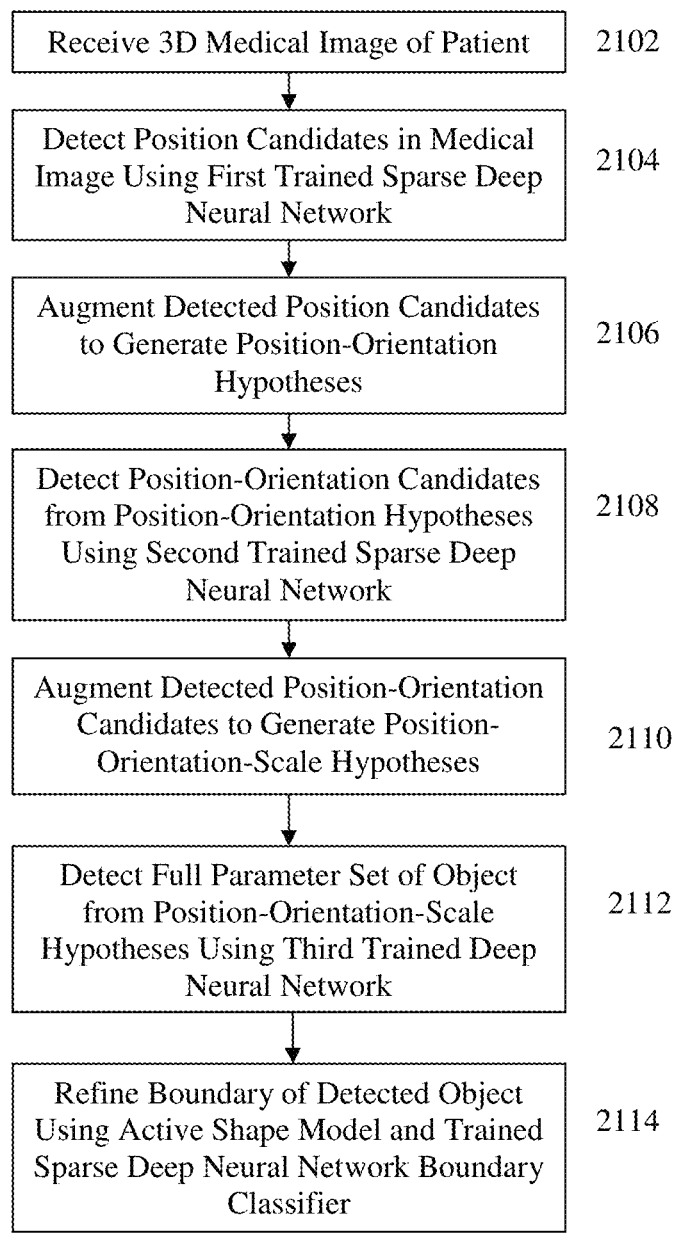
FIG. 21 illustrates a method of detecting and segmenting an anatomical object in a medical image using a series of trained sparse deep neural networks according to an embodiment of the present invention.
Figure 22:
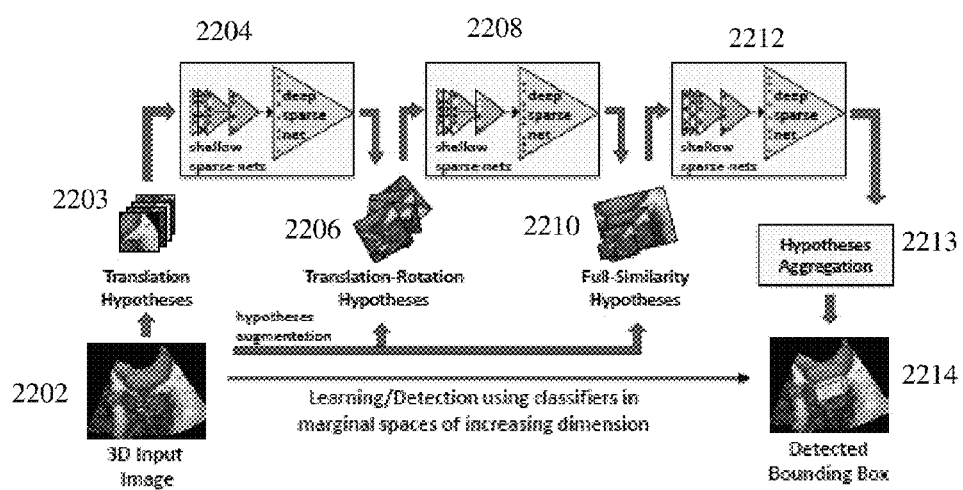
FIG. 22 illustrates a schematic visualization of the 3D object detection of steps 2102-2112 of FIG. 21.

FIG. 21 illustrates a method of detecting and segmenting an anatomical object in a medical image using a series of trained sparse deep neural networks according to an embodiment of the present invention. The method of FIG. 21 can be performed using a series of sparse adaptive deep neural networks (SADNN) trained using the iterative threshold enforced sparsity method of FIG. 15 or the re-weighted $L_1$ norm regularization method of FIG. 17. Steps 2102-2112 of FIG. 21 describe detection of the pose of the anatomical object in the 3D medical image, and step 2114 describes shape segmentation of the object in the 3D medical image non-rigid boundary deformation. FIG. 22 illustrates a schematic visualization of the 3D object detection of steps 2102-2112 of FIG. 21, and is described concurrently with these steps of FIG. 21.

Referring to FIG. 21, at step 2102, a 3D medical image of the patient is received. The 3D medical image can be acquired using any type of medical imaging modality, such as but not limited to CT, MRI, ultrasound, DynaCT, etc. The medical image can be received directly from an image acquisition device, such as a CT scanner, MRI scanner, ultrasound device, etc., or can be received by loading a previously acquired medical image of the patient from a memory or storage of a computer system. As shown in FIG. 22, the 3D input image 2202 is a 3D ultrasound image.

Returning to FIG. 21, at step 2104, position candidates are detected in the 3D medical image using a first trained sparse deep neural network. The first sparse deep neural network or first SADNN operates directly on the voxels of the 3D medical image, and not on handcrafted features extracted from the medical image. In an advantageous implementation, the filters of at least the first hidden layer of the first SADNN are sparse resulting from sparsification using iterative threshold enforced sparsity or re-weighted $L_1$ norm regularization during training of the first SADNN. Accordingly, for each image patch input to the first SADNN only a sparse adaptively determined sampling pattern of the voxels in the image may be needed to calculate the responses of the neurons in the first hidden layer of the first SADNN. As shown in block 2204 of FIG. 22, a first trained cascade of shallow sparse neural networks is used together with the first sparse deep neural network to detect position candidates. Image patches (translation hypotheses 2203) centered at voxels of the medical image are processed by the first cascade of shallow sparse neural networks to filter a number of negative hypotheses, and then the remaining image patches are input to the first trained SADNN, which calculates a number of position candidates in the medical image based on the input image patches. In an advantageous implementation, the first trained sparse deep neural network is a discriminative sparse deep neural network that inputs image patches centered at voxels of the medical image and calculates a probability for each image patch. A number of position candidates with highest probabilities calculated by the first trained deep neural network are kept.

Returning to FIG. 21, at step 2106, the position candidates detected by the first trained sparse deep neural network are augmented with orientation parameters to generate position-orientation hypotheses. For example, a plurality of position-orientation hypotheses can be generated for each detected position candidate by rotating each image patch centered at a position candidate to a plurality of possible orientations sampled from a predetermined range of orientations for the target anatomical object. The predetermined range of orientations can be determined by the range of orientations of the ground truth objects in a set of annotated training data. FIG. 22 shows translation-rotation hypotheses 2206. It is to be understood that "translation" and "position" are used herein interchangeably, and "orientation" and "rotation" are used herein interchangeably.

At step 2108, position-orientation candidates are detected from the position-orientation hypotheses using a second trained sparse deep neural network. The second sparse deep neural network or second SADNN operates directly on the voxels of image patches corresponding to position-orientation hypotheses. In an advantageous implementation, the filters of at least the first hidden layer of the second SADNN are sparse resulting from sparsification using iterative threshold enforced sparsity or re-weighted $L_1$ norm regularization during training of the second SADNN. Accordingly, for each image patch input to the second SADNN only a sparse adaptively determined sampling pattern of the voxels in the image may be needed to calculate the responses of the neurons in the first hidden layer of the second SADNN. As shown in block 2208 of FIG. 22, a second trained cascade of shallow sparse neural networks is used together with the second sparse deep neural network to detect the position-orientation candidates. The position-orientation hypotheses (translation-rotation hypotheses 2206) are processed by the second cascade of shallow sparse neural networks to filter a number of negative hypotheses, and then the remaining position-orientation hypotheses are input to the second trained SADNN, which calculates a number of position-orientation candidates in the medical image based on the input position-orientation hypotheses. In an advantageous implementation, the second trained sparse deep neural network is a discriminative sparse deep neural network that inputs image patches corresponding to the position-orientation hypotheses and calculates a probability for each image patch. A number of position-orientation candidates with highest probabilities calculated by the second trained deep neural network are kept.

Returning to FIG. 21, at step 2110, the position-orientation candidates detected by the second trained sparse deep neural network are augmented with scale parameters to generate position-orientation-scale hypotheses. For example, a plurality of position-orientation-scale (i.e., full similarity) hypotheses can be generated for each detected position-orientation candidate by scaling each image patch corresponding to a position-orientation candidate to a plurality of possible scales sampled from a predetermined range of scales for the target anatomical object. The predetermined range of scales can be determined by the range of scales of the ground truth objects in a set of annotated training data. FIG. 22 shows full similarity hypotheses 2210.

At step 2212, the full parameter set (position, orientation, and scale) of the target anatomical object is detected from the position-orientation-scale hypotheses using a third trained sparse deep neural network. The third sparse deep neural network or third SADNN operates directly on image patches of the medical image corresponding to position-orientation-scale hypotheses. In an advantageous implementation, the filters of at least the first hidden layer of the third SADNN are sparse resulting from sparsification using iterative threshold enforced sparsity or re-weighted $L_1$ norm regularization during training of the third SADNN. Accordingly, for each image patch input to the third SADNN only a sparse adaptively determined sampling pattern of the voxels in the image may be needed to calculate the responses of the neurons in the first hidden layer of the second SADNN. As shown in block 22012 of FIG. 22, a third trained cascade of shallow sparse neural networks is used together with the third sparse deep neural network to detect the position-orientation candidates. The full similarity hypotheses 2208 are processed by the third cascade of shallow sparse neural networks to filter out a number of negative hypotheses, and then the remaining full similarity hypotheses are input to the third trained SADNN, which calculates one or more fully similarity candidates in the medical image based on the input full similarity hypotheses. In an advantageous implementation, the third trained sparse deep neural network is a discriminative sparse deep neural network that inputs image patches corresponding to the full similarity hypotheses and calculates a probability for each image patch. In a possible implementation, the image patch corresponding to the full similarity hypothesis with the highest probability calculated by the third trained sparse deep neural network can be output as the detection result for the anatomical object. In another possible implementation, as shown in block 2213 of FIG. 22, a number of image patches corresponding to full similarity hypotheses with the highest probabilities can be aggregated or clustered to generate the final detection result for the anatomical object. As shown in image 2214 of FIG. 22, the final detection result defines a bounding box of the target anatomical structure.

Figure 23:
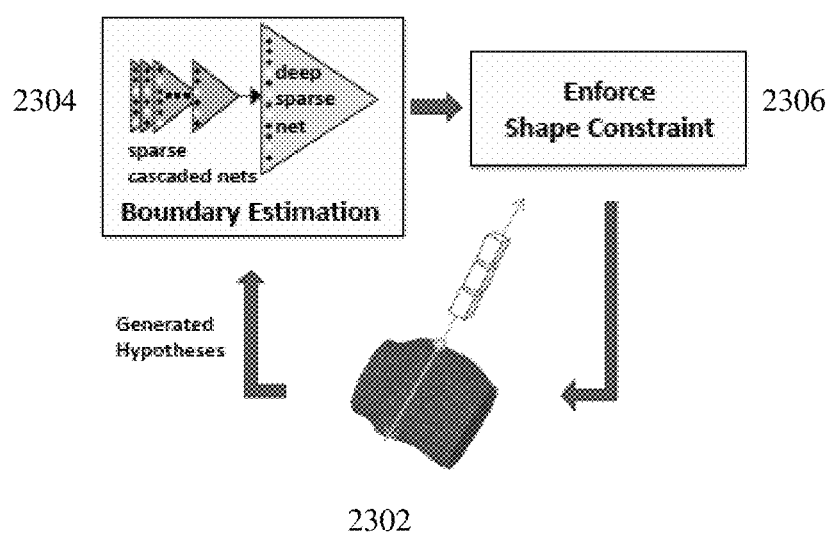
FIG. 23 illustrates a schematic visualization o boundary refinement using a trained sparse deep neural network boundary detector according to an embodiment of the present invention.

Returning to FIG. 21, at step 2114, a boundary of the detected anatomical object is refined using an active shape model (ASM) and a trained sparse deep neural network boundary detector. A mean model (e.g., 3D mesh) of the target anatomical object can be calculated from a set of annotated training data, and once the full parameter set (position, orientation, and scale) of the target anatomical object is detected in the medical image, the mean model can be rigidly registered to the medical image using the detected position, orientation, and scale of the target anatomical object, resulting in a segmented model of the target anatomical object in the medical image. Non-rigid local boundary refinement can be performed after the mean model is registered to the medical image. FIG. 23 illustrates a schematic visualization o boundary refinement using a trained sparse deep neural network boundary detector according to an embodiment of the present invention. As shown in FIG. 23, at 2302, for each boundary point of the segmented model of the target anatomical object a plurality of points are sampled in both directions along a line normal to the model surface. At 2304, image patches corresponding to the plurality of points sampled along the line normal to the model surface are evaluated using a trained SADNN boundary detector. The trained SADNN boundary detector calculates a probability for each point sampled along the normal line, and the boundary is refined by moving each boundary point to the point along the normal line having the highest probability. A negative filtering cascade of sparse shallow neural networks is also trained for the boundary detection, and is used to filter the image patches corresponding to the candidate boundary points along the normal line prior evaluation by the trained SADNN boundary detector. The SADNN boundary detector is trained using iterative threshold enforced sparsity or re-weighted $L_1$ norm regularization to automatically learn adaptive, sparse feature sampling patterns directly from the low-level image data. The boundary classification performed by the SADNN boundary detector can be in the joint position-orientation search space, with the position and orientation of each image patch given by corresponding sample along the normal for the respective shape point. Training of the SADNN boundary detector is performed using positive samples on the current ground truth boundary for each mesh point (aligned with the corresponding normal) and using negative samples at various distances from the boundary. The sparse adaptive patterns are important for efficiently identifying relevant anatomical structures when applying this classifier under arbitrary orientations.

At 2306, once the boundary of the model of the target anatomical structure is refined, a shape constraint is enforced on the refined model by projecting to a learned shape space of the target anatomical object using an active shape model. The learned shape space used to enforce the shape constraint is learned by estimating from the training data a linear shape subspace through principle components analysis, and during online boundary refinement, the current shape is projected to this subspace using the learned linear projector. As shown in FIG. 23, the steps of sampling boundary hypotheses along normal lines (2302), refining the model using the trained SADNN boundary detector (2304), and projecting the refined model to the learned shape space to enforce a shape constraint (2306) are performed in an iterative process. These steps can be iterated until the boundary converges and there are no more large deformations or for a predetermined number of iterations.

Figure 24:
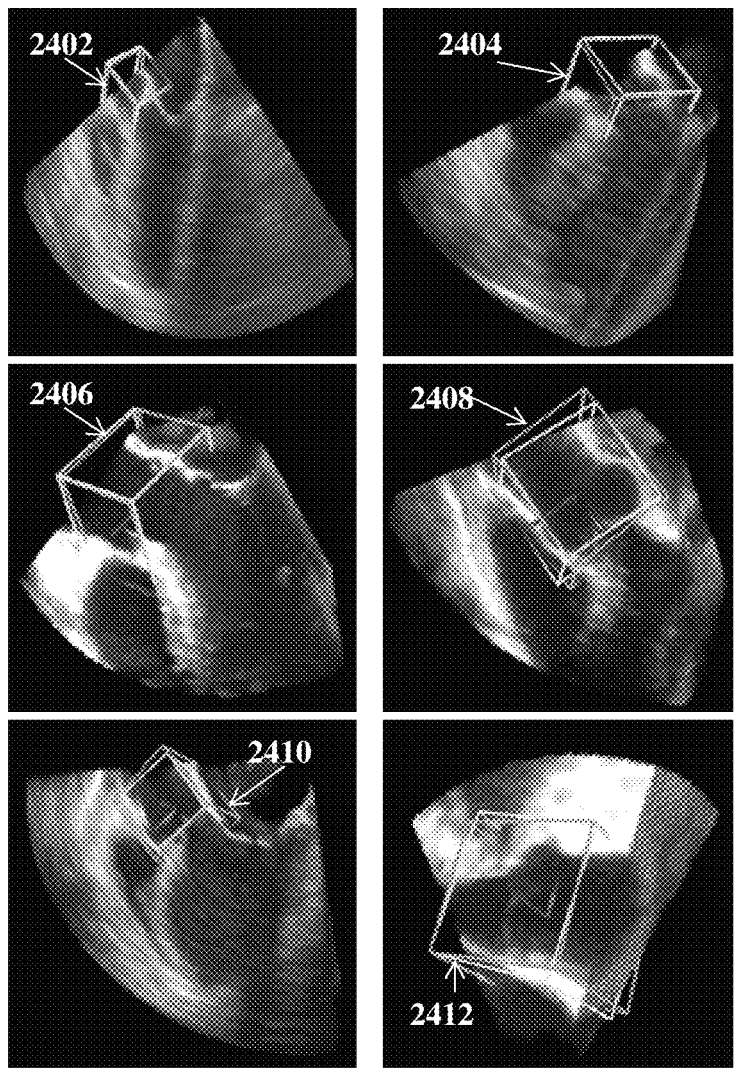
FIG. 24 illustrates exemplary results for detecting the aortic valve in 3D ultrasound images using the method of FIG. 21.
Figure 25:
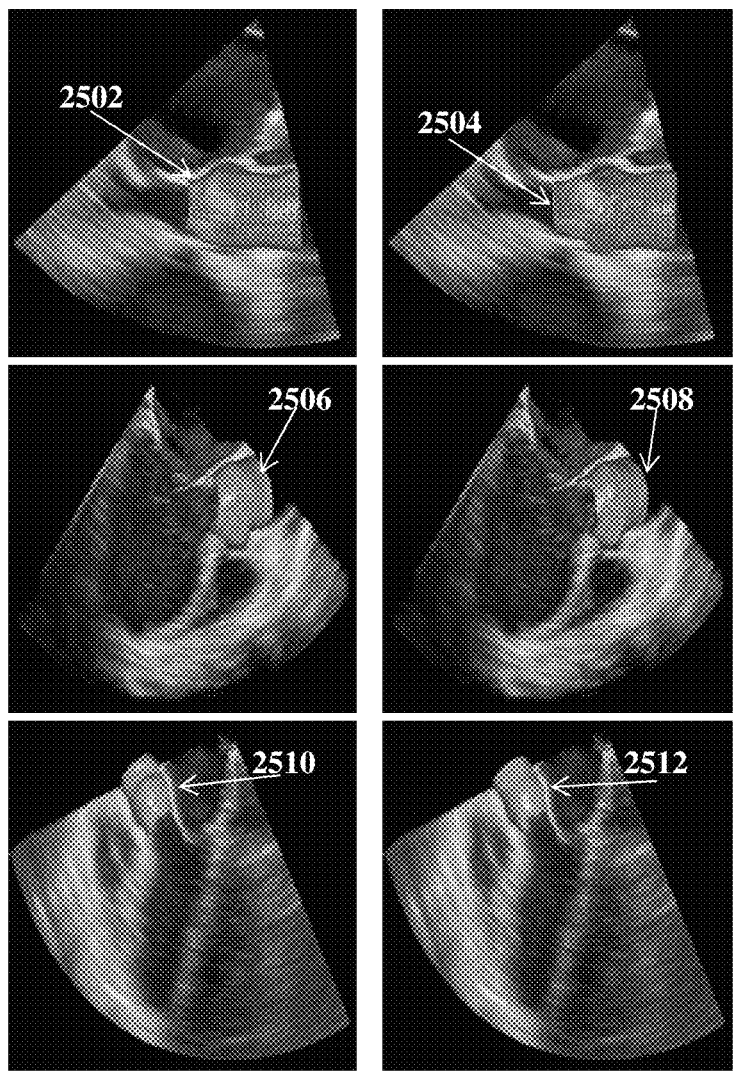
FIG. 25 illustrates exemplary results for segmenting the aortic valve in 3D ultrasound images using the method of FIG. 21.

The segmented 3D mesh of the target anatomical object and/or the bounding box detection result for the target anatomical object can be displayed on a display device of a computer. FIG. 24 illustrates exemplary results for detecting the aortic valve in 3D ultrasound images using the method of FIG. 21. In particular, FIG. 24 shows detected bounding boxes 2402, 2404, 2406, 2408, 2410, and 2412 showing the 3D pose (position, orientation, and scale) of the aortic valve in various 3D ultrasound images. FIG. 25 illustrates exemplary results for segmenting the aortic valve in 3D ultrasound images using the method of FIG. 21. In particular, FIG. 25 shows segmented 3D aortic valve meshes 2502, 2504, 2506, 2508, 2510, and 2512 in various 3D ultrasound images.

There are many applications of automatic landmark detection in medical image analysis, and various anatomical landmark detection methods have been proposed. Most landmark detection algorithms apply machine learning (e.g., support vector machines, random forest, or boosting algorithms) on a set of handcrafted image features (e.g., SIFT features or Haar wavelet features). However, in practice, there are still some landmark detection problems, such as detection of carotid artery bifurcation landmarks, that are too challenging to be accurately performed using existing methods. Deep learning has demonstrated success in computer vision with the capability to learn powerful image features from a large training set. However, there are several challenges in applying deep learning to 3D landmark detection. The input to a neural network classifier is normally an image patch, which increases dramatically in size from 2D to 3D. For example, a patch of 32×32 pixels corresponds to an input of 1024 dimensions. However, a 32×32×32 3D patch contains 32,768 voxels. Such a big input feature vector creates several challenges. First, the computation time of a deep neural network is often too slow for a real clinical application. The most widely used and robust approach for object detection is the sliding-window based approach, in which the trained classifier is tested on each voxel in the volume. Evaluating a deep network on a large volume may take several minutes. Second, a network with a bigger input vector requires more training data. With enough training samples, deep learning has demonstrated impressive performance gain over other methods. However, the medical imaging community often struggles with limited training samples due to the difficulty in generating and sharing images. Several approaches can address or at least mitigate the issue of limited training samples. One approach is to reduce the patch size. For example, if we reduce the patch size from 32×32×32 voxels to 16×16×16, we can significantly reduce the input dimension by a factor of eight. However, a small patch may not contain enough information for classification. Alternatively, instead of sampling of a 3D patch, we can sample on three orthogonal planes (or even a 2D patch with a random orientation). Although this can effectively reduce the input dimension, there is a concern on how much 3D information is contained in 2D planes.

Embodiments of the present invention utilize deep learning for 3D anatomical landmark detection. Embodiments of the present invention provide significantly accelerated detection speed, resulting in an efficient method that can detect an anatomical landmark in less than one second. Embodiments of the present invention utilize apply a two-stage classification strategy. In the first stage, a shallow network is trained with only one small hidden layer (e.g., with 64 hidden nodes). This network is applied to test all voxels in the volume in a sliding-window process to generate a number of candidates (e.g., 2000) for the second stage of classification. The second network is much bigger. In exemplary embodiment, the second network is a deep neural network that has three hidden layers, each with 2000 hidden nodes to obtain more discriminative power. The weights of a node in the first hidden layer are often treated as a filter (3D in this case). The response of the first hidden layer over the volume can be calculated as a convolution with the filter. Here, the neighboring patches are shifted by only one voxel; however, the response needs to be recalculated from scratch. In an embodiment of the present invention, the weights are approximated as separable filters using tensor decomposition. Therefore, a direct 3D convolution is decomposed as three one-dimensional convolutions along the x, y, and z axes, respectively. Previously, such approximation has been exploited for 2D classification problems. However, in 3D, the trained filters are more difficult to be approximated as separable filters. In an embodiment of the present invention, the training cost function is modified to enforce smoothness of the filters so that they can be approximated with high accuracy. The second big network is only applied on a small number of candidates that have little correlation. The separable filter approximation does not help. However, many weights in a big network are close to zero. In an embodiment of the present invention, L1-norm regularization is added to the cost function to drive majority of the weights (e.g., 90%) to zero, resulting in a sparse network with increased classification efficiency.

The power of deep learning is in the automatic learning of discriminative image representation (i.e., image features). According to an advantageous embodiment of the present invention, instead of using the trained deep neural network as a classifier, we can use the responses at each layer (including the input layer, all hidden layers, and the output layer) as features and feed them into other machine learning classifiers, such as a boosting classifier. After years of feature engineering, some handcrafted features have considerable discriminative power for some applications and they may be complimentary to deeply learned features. In an advantageous embodiment, combining deeply learned features and Haar wavelet features can significantly reduce detection failures.

Figure 26:
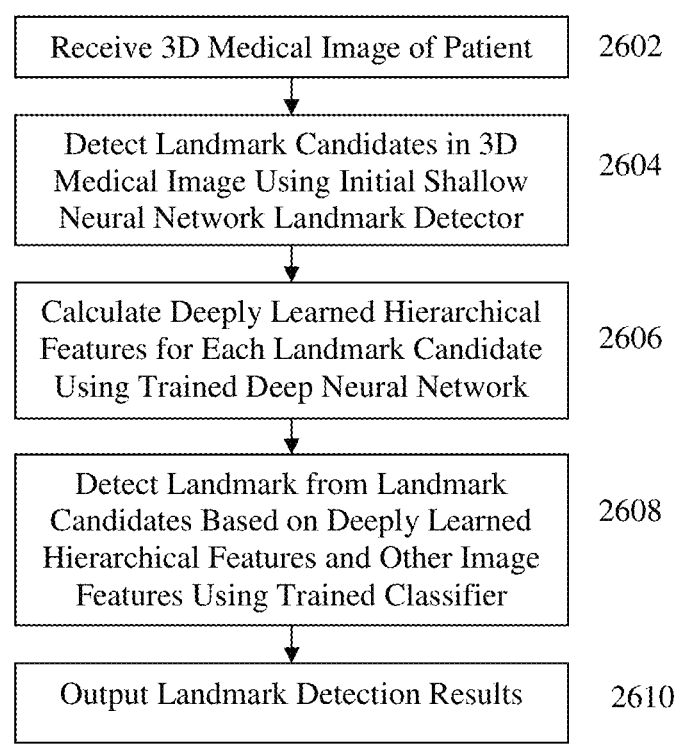
FIG. 26 illustrates a method for automated anatomical landmark detection in a 3D medical image according to an embodiment of the present invention.

FIG. 26 illustrates a method for automated anatomical landmark detection in a 3D medical image according to an embodiment of the present invention. At step 2602, a 3D medical image of the patient is received. The 3D medical image can be acquired using any type of medical imaging modality, such as but not limited to CT, MRI, ultrasound, DynaCT, etc. The medical image can be received directly from an image acquisition device, such as a CT scanner, MRI scanner, ultrasound device, etc., or can be received by loading a previously acquired medical image of the patient from a memory or storage of a computer system.

At step 2604, landmark candidates for a target anatomical landmark are detected in the 3D medical image using an initial shallow neural network landmark detector. In an advantageous implementation, the shallow neural network is trained with only one small hidden layer (e.g., with 64 hidden nodes). The trained shall neural network can be applied to test all voxels in the 3D medical image in a sliding-window process to generate a number of candidates (e.g., 2000) for the second stage of classification.

A fully connected multilayer perceptron (MLP) neural network is a layered architecture. Suppose the input is a $n_0$-dimensional vector $[X_1^0, X_2^0, \ldots, X_{n_0}^0]$. The response of a node $X_j^1$ of the first hidden layer is:

$$X_j^1 = g(\Sigma_{i=1}^{n_0} W_{i,j}^0 X_i^0 + b_j^0), \quad (9)$$

for $j=1, 2, \ldots n_1$ ($n_1$ is the number of nodes in the first hidden layer). Here, $g(\bullet)$ is a nonlinear function, which can be sigmoid, hypo-tangent, restricted linear unit (ReLU), or other forms. In an advantageous implementation, the sigmoid function is used. $W_{i,j}^0$ is a weight and $b_j^0$ is a bias term. If we denote $X^0 = [1, X_1^0, \ldots, X_n^0]$ and $W_j^0 = [b_j^0, W_{1,j}^0, \ldots, W_{n,j}^0]$, Equation (9) can be re-written as $X_j^1 = g((W_j^0)^T X^0)$. Multiple layers can be stacked together using Equation (9) as a building block. However, the initial landmark detector in step 2604 is a shallow network with only one hidden layer. For a binary classification problem, such landmark detection, the output of the network can be a single node $\hat{X}$. Suppose there are L−1 hidden layers, the output of the neural network is $\hat{X} = g((W^L)^T X^L)$. During network training, we require the output to match the class label Y (with 1 for a positive class and 0 for negative) by minimizing the squared error:

$$E = \|Y - \hat{X}\|^2. \quad (10)$$

In object detection using a sliding window based approach, for each position hypothesis, an image patch (with a pre-defined size) centered at the position hypothesis is cropped. The patch intensities are then serialized into a vector as the input to calculate response $\hat{X}$. After testing an image patch, we shift the image patch by one voxel (e.g., to the right) and repeat the above process again. Such a naive implementation is time consuming. Returning to Equation (9), the weights of a node in the first hidden layer can be treated as a filter. The first term of the response is a dot-product of the filter and the image patch intensities. Shifting the patch over the whole volume is equivalent to performing convolution using the filter. Therefore, alternatively, we can perform convolution using each filter $W_j^0$ for $j=1, 2, \ldots, n_1$ and cache the response maps. During object detection, we can use the cached maps to retrieve the response of the first hidden layer.

Even though such an alternative approach does not save computations time, it provides a hint for speed-up. With a bit of abuse of symbols, suppose $W_{x,y,z}$ is a 3D filter with size $n_x \times n_y \times n_z$. We can further assume that $W_{x,y,z}$ is separable, which means the we can find one dimensional vectors, $W_x$, $W_y$, $W_z$, such that:

$$W_{x,y,z}(i,j,k) = W_x(i) \cdot W_y(j) \cdot W_z(k) \quad (11)$$

for any $i \in [1, n_x]$, $j \in [1, n_y]$, and $k \in [1, n_z]$. The convolution of the volume with $W_{x,y,z}$ is equivalent to three sequential convolutions with $W_x$, $W_y$, $W_z$, respectively. Sequential convolution with one dimensional filters is much more efficient than direct convolution with a 3D filter, especially for a large filter. However, in reality, Equation (11) is just an approximation to filters learned by a neural network and such a rank−1 approximation is poor in general. In practice, we search for a filter bank with S sets of separable filters to approximate the original filter as:

$$W_{x,y,z} \approx \Sigma_{s=1}^{S} W_x^s \cdot W_y^s \cdot W_z^s. \quad (12)$$

Please note, with a sufficient number of separable filters (e.g., $S \geq \min\{n_x, n_y, n_z\}$), the original filter can be reconstructed perfectly.

To achieve detection efficiency, $n_1 \times S$ filtered response maps need to be cached. If the input volume is big (the size of a typical CT scan in the present inventors' dataset is about 300 MB) and $n_1$ is relatively large (e.g., 64 or more), the cached response maps consume large amount of memory. Fortunately, the learned filters $W_1^0, \ldots, W_{n_1}^0$ often have strong correlation (i.e., a filter can be reconstructed by a linear combination of other filters). We do not need to maintain different filter banks for each $W_i^0$. The separable filters in reconstruction can be drawn from the same bank, $$W_i^0 \approx \Sigma_{s=1}^S c_{i,s} \cdot W_x^s \cdot W_y^s \cdot W_z^s. \quad (13)$$

Here, $c_{i,s}$ is the combination coefficient, which is specific for each filter $W_i^0$. However, $W_x^s$, $W_y^s$, and $W_z^s$ are shared by all filters. Equation (13) is a rank-S decomposition of a 4D tensor $[W_1^0, W_2^0, \ldots, W_{n_1}^0]$, which can be solve using known techniques. Using 4D tensor decomposition, the volume only needs to be convolved S times (instead of $n_1 \cdot S$ times using 3D tensor decomposition) and S response maps need to be cached. Suppose the input volume has $N_x \times N_y \times N_z$ voxels. For each voxel, $n_x n_y n_z$ multiplications need to be performed using the original sliding window based approach. To calculate the response of the hidden layer with $n_1$ nodes, the total number of multiplications is $n_1 n_x n_y n_z N_x N_y N_z$. Using the proposed 4D tensor decomposition approach, $(n_x + n_y + n_z) N_x N_y N_z$ multiplications need to be done to perform convolution with one set of separable filters, and there are S sets of separable filters. To calculate the response of the hidden layer node, we need to combine S response using Equation (13). The total number of multiplications is $S(n_x + n_y n_z + n_1) N_x N_y N_z$. Suppose S=32, $n_1$=64, the speed up is 103 times for a 15×15×15 image patch.

To achieve significant speed-up and save memory footprint, S needs to be reduced as much as possible. However, the present inventors have determined that, with a small S (e.g., 32), it is more difficult to approximate 3D filters than 2D filters. Non-linear functions g(•) are exploited in neural networks to bound the response to a certain range (e.g., [0, 1] using the sigmoid function). Many nodes are saturated (with an output close to 0 or 1) and once a node is saturated, its response is not sensitive to the change of the weights. Therefore, a weight can take an extremely large value, resulting in a non-smooth filter. According to an advantageous embodiment of the present invention, the objective function in Equation (10) can be modified to encourage the network to generate smooth filters:

$$E = \|Y - \hat{X}\|^2 + \alpha \Sigma_{i=1}^{n_1} \|W_i^0 - \overline{W_i^0}\|^2. \quad (14)$$

Here, $\overline{W_i^0}$ is the mean value of the weights of filter $W_i^0$. So, the second term measures the variance of the filter weights. Parameter $\alpha$ (often takes a small value, e.g., 0:001) keeps a balance between of two terms in the objective function.

In an advantageous implementation, the training of the initial shallow network detector is as follows: 1) Train a network using the objective function of Equation (14). In an exemplary implementation, the shallow network is trained directly with back-propagation. 2) Approximate the learned filters using a filter bank with S (e.g., S=32) separable filters to minimize the error of Equation (13). This process may be iterated a predetermined number of times (e.g., three times). In the first iteration, the network weights and filter bank are initialized randomly. However, in the following iterations, they are both initialized with the optimal value from the previous iteration.

Previously, separable filter approximation has been exploited for 2D classification problems. However, 3D filters are more difficult to approximate accurately with a small filter bank. Accordingly, embodiments of the present invention modify the objective function to encourage the network to generate smooth filters with higher separability. Furthermore, embodiments of the present invention also iteratively re-train the network to compensate for the loss of accuracy due to approximation.

Using the trained initial shallow network detector, all voxels in the received 3D medical image can be efficiently tested, and each voxel is assigned a detection score by the shallow network detector. A predetermined number (e.g., 2000) of landmark candidates with the largest detection scores are preserved. The number of preserved candidates is tuned to have a high probability to include the correct detection (e.g., a hypotheses within one-voxel distance to the ground truth). However, most of the preserved candidates are still false positives.

Returning to FIG. 26, at step 2606, deeply learned hierarchical features are calculated for each of the detected landmark candidates using a trained deep neural network. In this second classification stage, a deep neural network is trained to further reduce the false positives in the preserved candidates result from the first classification stage (step 2604). The classification problem is now much tougher and a shallow network does not work well. In an advantageous implementation, a deep neural network with three hidden layers, each with 2000 nodes is used.

Even though only a small number of candidates need to be classifier in this stage, the computation may still take some time since the network is now much bigger. Since the preserved candidates are often scattered over the whole volume, separable filter decomposition as used in the initial detection does not help to accelerate the classification. After checking the values of the learned weights of this deep network, the present inventors have observed that most of weights were very small, close to zero. That means many connections in the network can be removed without scarifying classification accuracy. In an advantageous implementation, we apply L1-norm regularization to enforce sparse connection:

$$E = \|Y - \hat{X}\|^2 + \beta \Sigma_{j=1}^L \Sigma_{i=1}^{n_j} \|W_i^j\|. \quad (15)$$

Alternative ways can also be exploited to simplify a network. For example, threshold enforced sparsity can be performed, as described above. Using the L1-norm, many weights naturally converge to zero during training of the network. Parameter $\beta$ can be used to tune the number of zero weights. The higher $\beta$ is, the more weights converge to zero. In an advantageous implementation, 90% of weighs can be set to zero, without deteriorating the classification accuracy. Thus, a speed up of the classification by ten times can be achieved. The proposed acceleration technologies can be applied to different neural network architectures, e.g., a multilayer perceptron (MLP) or a convolutional network (CNN). In one exemplary implementation, the MLP was used. In another exemplary implementation, the CNN was used and achieved similar detection accuracy. In and advantageous implementation, the deep network is trained using the denoising auto-encoder criterion.

To train a robust deep neural network based landmark detector on a limited training samples, the input image patch size must be controlled. In an advantageous implementation, the present inventors have found that an image patch size of 15×15×15 achieved a good trade-off between detection speed and accuracy. However, a small patch has a limited field-of-view, thereby may not capture enough information for classification. According to an advantageous embodiment, image patches for each of the landmark candidates can be extracted on an image pyramid with multiple resolutions. A small patch in a low-resolution volume corresponds to a much larger field-of-view at the original resolution. In an exemplary implantation, an image pyramid is built with three resolutions (1-mm, 2-mm, and 4-mm resolution, respectively) from the received 3D medical image, and the trained deep neural network is applied to image patches at each resolution for each landmark candidate.

Deep learning automatically learns a hierarchical representation of the input data. Representation at different hierarchical levels may provide complementary information for classification. According to an advantageous embodiment of the present invention, the trained deep neural network is applied to all of the landmark candidates (at multiple resolutions), resulting in a set of neural network features $r_i^j$ for each landmark candidate, where $r_i^j$ is the response of node i at layer j. The set of neural network feature can include the response of the neural network node for an image patch at each resolution level.

Returning to FIG. 26, at step 2608, the landmark is detected from the landmark candidates based on the deeply learned (neural network) features and other features extracted from the 3D medical image using a trained classifier. In an advantageous embodiment, a trained probabilistic boosting tree (PBT) classifier is used to combine the different types of features. A PBT is a combination of a decision tree and boosting, by replacing the weak classification node in a decision tree with a strong AdaBoost classifier. In an advantageous implementation, the feature pool includes two types of features: Haar wavelet features ($h_1, h_2, \ldots, h_m$) and neural network features $r_i^j$, where $r_i^j$ is the response of node i at layer j. If j=0, $r_j^0$ is an input node, representing the image intensity of a voxel in the image patch. The last neural network feature is the response of the output node of the deep neural network, which is the classification score by the network. This feature is the strongest feature and is always the first feature selected by the AdaBoost algorithm. The neural network features and the Haar wavelet features for a particular landmark candidate can include neural network features resulting from applying the deep neural network at multiple resolutions of the image pyramid and Haar wavelet features extracted for the landmark candidate at multiple resolutions of the image pyramid. It is to be understood that the present invention is not limited to Haar features, and other handcrafted features, such as SIFT features or steerable features can be used as well. The trained PBT classifier inputs neural network features and Haar wavelet features from the feature pool for each candidate and calculates a probability score for each landmark candidate based on the features. The landmark candidate having the highest probability score is selected as the detected anatomical landmark.

At step 2610, the landmark detection results are output. In particular, the detected landmark can be displayed on a display device of a computer system.

Figure 27:
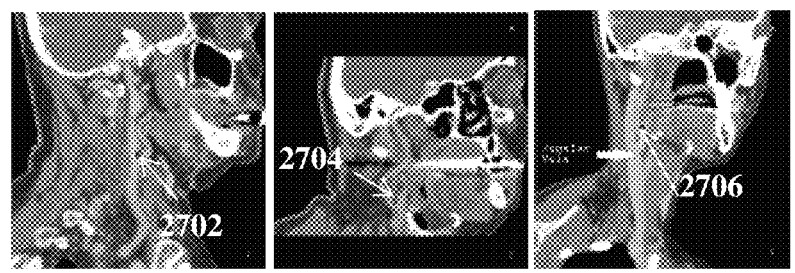
FIG. 27 illustrates exemplary detection results for automatic carotid artery bifurcation landmark detection in head-neck CT scans using the method of FIG. 26.

In an advantageous embodiment, the method of FIG. 26 is applied to automatic carotid artery bifurcation landmark detection in head-neck CT scans. The carotid artery is the main vessel supplying oxygenated blood to the head and neck. The common carotid artery originates from the aortic arch and runs up toward the head before bifurcating to the external carotid artery (supplying blood to face) and internal carotid artery (supplying blood to brain). Examination of the carotid artery helps to assess the stroke risk of a patient. Automatic detection of this bifurcation landmark provides a seed point for centerline tracing and lumen segmentation, thereby potentially making the carotid artery examination automatic. However, the internal/external carotid arteries further bifurcate to many branches and there are other vessels (e.g., vertebral arteries and jugular veins) present nearby, which cause confusion to automatic detection algorithms. FIG. 27 illustrates exemplary detection results for automatic carotid artery bifurcation landmark detection in head-neck CT scans using the method of FIG. 26. In particular, FIG. 27 shows detection results 2702, 2704, and 2706 for the right carotid artery bifurcation in various head-neck CT scans.

Figure 28:
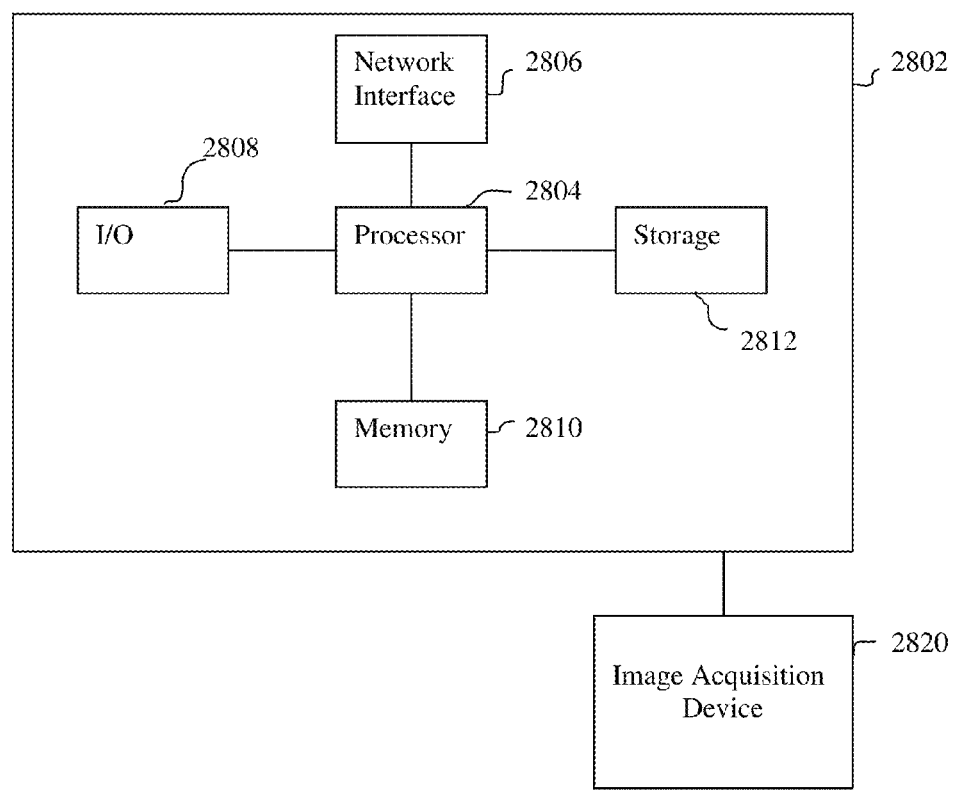
FIG. 28 is a high-level block diagram of a computer capable of implementing the present invention.

The above-described methods can be implemented on a computer using well-known computer processors, memory units, storage devices, computer software, and other components. A high-level block diagram of such a computer is illustrated in FIG. 28. Computer 2802 contains a processor 2804, which controls the overall operation of the computer 2802 by executing computer program instructions which define such operation. The computer program instructions may be stored in a storage device 2812 (e.g., magnetic disk) and loaded into memory 2810 when execution of the computer program instructions is desired. Thus, the steps of the methods of FIGS. 1, 4, 5, 6, 9, 13, 15-23, and 26 may be defined by the computer program instructions stored in the memory 2810 and/or storage 2812 and controlled by the processor 2804 executing the computer program instructions. An image acquisition device 2820, such as an MR scanning device, CT scanning device, ultrasound device, x-ray image acquisition device, etc., can be connected to the computer 2802 to input image data to the computer 2802. It is possible to implement the image acquisition device 2820 and the computer 2802 as one device. It is also possible that the image acquisition device 2820 and the computer 2802 communicate wirelessly through a network. In a possible embodiment, the computer 2802 may be located remotely from the image acquisition device 2820, and the computer 2802 may perform method steps as part of a server or cloud based service. The computer 2802 also includes one or more network interfaces 2806 for communicating with other devices via a network. The computer 2802 also includes other input/output devices 2808 that enable user interaction with the computer 2802 (e.g., display, keyboard, mouse, speakers, buttons, etc.). Such input/output devices 2808 may be used in conjunction with a set of computer programs as an annotation tool to annotate volumes received from the image acquisition device 2820. One skilled in the art will recognize that an implementation of an actual computer could contain other components as well, and that FIG. 28 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for anatomical object detection in a 3D medical image of a patient, comprising:
receiving a 3D medical image of a patient including a target anatomical object; and
detecting a 3D pose of the target anatomical object in the 3D medical image in a series of marginal parameter spaces of increasing dimensionality using a respective trained sparse deep neural network for each of the marginal parameter spaces, wherein each respective trained sparse deep neural network inputs hypothesis image patches in the respective marginal parameter space, samples voxels in each hypothesis image patch in a sparse sampling pattern adaptively learned during training of the respective trained sparse deep neural network, and calculates, for each hypothesis image patch, a probability that the hypothesis image patch is an image patch of the target anatomical object in the respective marginal parameter space based on the voxels sampled in the hypothesis image patch in the sparse sampling pattern.

2. The method of claim 1, wherein at least one of the respective trained sparse deep neural networks is trained by:
training a deep neural network by learning parameters of a respective filter for each of a plurality of neurons in each of a plurality of layers of the deep neural network, wherein the parameters of each respective filter include a bias and a plurality of weights that weight node outputs of the nodes of a previous one of the plurality of layers; and
sparsifying the weights of the filters for at least one layer of the trained deep neural network.

3. The method of claim 2, wherein sparsifying the weights of the filters for at least one layer of the trained deep neural network comprises:
reducing a number of non-zero weights in each filter for the at least one layer in the trained deep neural network by setting a predetermined percentage of non-zero weights with lowest magnitudes in each filter equal to zero; and
retraining the deep neural network with only the remaining non-zero weights in each filter for the at least one layer to refine the bias and the remaining non-zero weights in each filter for the at least one layer to recover from an effect of reducing the number of non-zero weights.

4. The method of claim 3, wherein sparsifying the weights of the filters for at least one layer of the trained deep neural network further comprises:
repeating the reducing and retraining steps in each of a plurality of iterations.

5. The method of claim 4, wherein sparsifying the weights of the filters for at least one layer of the trained deep neural network further comprises:
performing, in each iteration, a normalization to preserve an $L_1$-norm for each filter for the at least one layer.

6. The method of claim 4, wherein repeating the reducing and retraining steps in each of a plurality of iterations comprises:
repeating the reducing and retraining steps until a target sparsity degree is reached.

7. The method of claim 2, wherein the at least one layer is a first hidden layer of the deep neural network.

8. The method of claim 2, wherein sparsifying the weights of the filters for at least one layer of the trained deep neural network comprises:
performing re-weighted L1-norm regularization on the weights of the filters for the at least one layer of the trained deep neural network, wherein the re-weighted L1-norm regularization drives a plurality of non-zero weights of the filters for the at least one layer to zero; and
training a sparse deep neural with only the remaining non-zero weights in the filters for the at least one layer.

9. The method of claim 1, wherein detecting a 3D pose of the target anatomical object in the 3D medical image in a series of marginal parameter spaces of increasing dimensionality using a respective trained sparse deep neural network for each of the marginal parameter spaces comprises, for each of the marginal parameter spaces:
filtering hypothesis image patches in that marginal parameter space using a respective cascade of trained shallow sparse neural networks to eliminate a plurality of negative hypothesis image patches; and
evaluating each of the remaining hypothesis image patches in that marginal parameter space using the respective trained sparse deep neural network to determine a classification score for each of the remaining hypothesis image patches in that marginal parameter space.

10. The method of claim 9, wherein the respective cascade of trained shallow sparse neural networks for each marginal parameter space is trained by sequentially adding shallow sparse neural networks to the cascade until a balanced set of positive and negative training samples is achieved for training the respective sparse deep neural network.

11. The method of claim 1, further comprising:
rigidly registering a mean model of the target anatomical object to the 3D medical mage using the detected 3D pose of the target anatomical object in the 3D medical image;
refining the model of the target anatomical structure in the 3D medical image using a trained sparse deep neural network boundary detector applied to image patches corresponding to sampling points along a line normal to a surface of the model at each point on the surface of the model; and
projecting the refined model of the target anatomical object in the 3D medical image to a learned shape space of the target anatomical object.

12. The method of claim 1, wherein the series of marginal parameter spaces comprises a position parameter space, a position-orientation parameter space, and a position-orientation-scale parameter space.

13. The method of claim 12, wherein detecting a 3D pose of the target anatomical object in the 3D medical image in a series of marginal parameter spaces of increasing dimensionality using a respective trained sparse deep neural network for each of the marginal parameter spaces comprises:
detecting position candidates in the 3D medical image using a first cascade of trained sparse shallow neural networks to filter image patches centered at each of a plurality of voxels in the medical image and a first trained sparse deep neural network to evaluate image patches not eliminated by the first cascade;
generating position-orientation hypotheses based on the detected position candidates;
detecting position-orientation candidates in the 3D medical image using a second cascade of trained sparse shallow neural networks to filter image patches corresponding to the position-orientation hypotheses and a second trained sparse deep neural network to evaluate image patches corresponding position-orientation hypotheses not eliminated by the second cascade;
generating position-orientation-scale hypotheses based on the detected position-orientation candidates; and
detecting the pose of the target anatomical object in the 3D medical image using a third cascade of trained sparse shallow neural networks to filter image patches corresponding to the position-orientation-scale hypotheses and a third trained sparse deep neural network to evaluate image patches corresponding position-orientation-scale hypotheses not eliminated by the third cascade.

14. A method of automated anatomical landmark detection in a 3D medical image, comprising:
   detecting a plurality of landmark candidates for a target anatomical landmark in the 3D medical image using an initial shallow neural network detector;
   calculating deeply learned features for each of the plurality of landmark candidates using a trained deep neural network, wherein the trained deep neural network inputs respective image patches for the plurality of landmark candidates, samples voxels in each respective image patch in a sparse sampling pattern adaptively learned during training of the trained deep neural network, and calculates the deeply learned features for the plurality of landmark candidates based on the voxels sampled in the respective image patches in the sparse sampling pattern; and
   detecting the target anatomical landmark in the 3D medical image from the plurality of landmark candidates based on the deeply learned features for each of the plurality of landmark candidates and other image-based features extracted from the 3D medical image using a trained classifier.

15. The method of claim 14, wherein the trained classifier is a probabilistic boosting tree (PBT) classifier, and the other image based-features are Haar wavelet features.

16. An apparatus for anatomical object detection in a 3D medical image of a patient, comprising:
   a processor; and
   a memory storing computer program instructions, which when executed by the processor cause the processor to perform operations comprising:
   receiving a 3D medical image of a patient including a target anatomical object; and
   detecting a 3D pose of the target anatomical object in the 3D medical image in a series of marginal parameter spaces of increasing dimensionality using a respective trained sparse deep neural network for each of the marginal parameter spaces, wherein each respective trained sparse deep neural network inputs hypothesis image patches in the respective marginal parameter space, samples voxels in each hypothesis image patch in a sparse sampling pattern adaptively learned during training of the respective trained sparse deep neural network, and calculates, for each hypothesis image patch, a probability that the hypothesis image patch is an image patch of the target anatomical object in the respective marginal parameter space based on the voxels sampled in the hypothesis image patch in the sparse sampling pattern.

17. The apparatus of claim 16, wherein at least one of the respective trained sparse deep neural networks is trained by:
   training a deep neural network by learning parameters of a respective filter for each of a plurality of neurons in each of a plurality of layers of the deep neural network, wherein the parameters of each respective filter include a bias and a plurality of weights that weight node outputs of the nodes of a previous one of the plurality of layers; and
   sparsifying the weights of the filters for at least one layer of the trained deep neural network.

18. The apparatus of claim 17, wherein sparsifying the weights of the filters for at least one layer of the trained deep neural network comprises:
   reducing a number of non-zero weights in each filter for the at least one layer in the trained deep neural network by setting a predetermined percentage of non-zero weights with lowest magnitudes in each filter equal to zero; and
   retraining the deep neural network with only the remaining non-zero weights in each filter for the at least one layer to refine the bias and the remaining non-zero weights in each filter for the at least one layer to recover from an effect of reducing the number of non-zero weights.

19. The apparatus of claim 18, wherein sparsifying the weights of the filters for at least one layer of the trained deep neural network further comprises:
   performing a normalization to preserve an $L_1$-norm for each filter for the at least one layer.

20. The apparatus of claim 17, wherein the at least one layer is a first hidden layer of the deep neural network.

21. The apparatus of claim 17, wherein sparsifying the weights of the filters for at least one layer of the trained deep neural network comprises:
   performing re-weighted L1-norm regularization on the weights of the filters for the at least one layer of the trained deep neural network, wherein the re-weighted L1-norm regularization drives a plurality of non-zero weights of the filters for the at least one layer to zero; and
   training a sparse deep neural with only the remaining non-zero weights in the filters for the at least one layer.

22. The apparatus of claim 16, wherein detecting a 3D pose of the target anatomical object in the 3D medical image in a series of marginal parameter spaces of increasing dimensionality using a respective trained sparse deep neural network for each of the marginal parameter spaces comprises:
   filtering hypothesis image patches in each of the marginal parameter spaces using a respective cascade of trained shallow sparse neural networks to eliminate a plurality of negative hypothesis image patches; and
   evaluating each of the remaining hypothesis image patches in each of the marginal parameter spaces using the respective trained sparse deep neural network to determine a classification score for each of the remaining hypothesis image patches in that marginal parameter space.

23. The apparatus of claim 16, wherein the operations further comprise:
   rigidly registering a mean model of the target anatomical object to the 3D medical mage using the detected 3D pose of the target anatomical object in the 3D medical image;
   refining the model of the target anatomical structure in the 3D medical image using a trained sparse deep neural network boundary detector applied to image patches corresponding to sampling points along a line normal to a surface of the model at each point on the surface of the model; and
   projecting the refined model of the target anatomical object in the 3D medical image to a learned shape space of the target anatomical object.

24. The apparatus of claim 16, wherein the series of marginal parameter spaces comprises a position parameter space, a position-orientation parameter space, and a position-orientation-scale parameter space.

25. The apparatus of claim 24, wherein detecting a 3D pose of the target anatomical object in the 3D medical image in a series of marginal parameter spaces of increasing dimensionality using a respective trained sparse deep neural network for each of the marginal parameter spaces comprises:

detecting position candidates in the 3D medical image using a first cascade of trained sparse shallow neural networks to filter image patches centered at each of a plurality of voxels in the medical image and a first trained sparse deep neural network to evaluate image patches not eliminated by the first cascade;

generating position-orientation hypotheses based on the detected position candidates;

detecting position-orientation candidates in the 3D medical image using a second cascade of trained sparse shallow neural networks to filter image patches corresponding to the position-orientation hypotheses and a second trained sparse deep neural network to evaluate image patches corresponding position-orientation hypotheses not eliminated by the second cascade;

generating position-orientation-scale hypotheses based on the detected position-orientation candidates; and detecting the pose of the target anatomical object in the 3D medical image using a third cascade of trained sparse shallow neural networks to filter image patches corresponding to the position-orientation-scale hypotheses and a third trained sparse deep neural network to evaluate image patches corresponding position-orientation-scale hypotheses not eliminated by the third cascade.

26. An apparatus for automated anatomical landmark detection in a 3D medical image, comprising:

a processor; and a memory storing computer program instructions, which when executed by the processor cause the processor to perform operations comprising:

detecting a plurality of landmark candidates for a target anatomical landmark in the 3D medical image using an initial shallow neural network detector;

calculating deeply learned features for each of the plurality of landmark candidates using a trained deep neural network, wherein the trained deep neural network inputs respective image patches for the plurality of landmark candidates, samples voxels in each respective image patch in a sparse sampling pattern adaptively learned during training of the trained deep neural network, and calculates the deeply learned features for the plurality of landmark candidates based on the voxels sampled in the respective image patches in the sparse sampling pattern; and detecting the target anatomical landmark in the 3D medical image from the plurality of landmark candidates based on the deeply learned features for each of the plurality of landmark candidates and other image-based features extracted from the 3D medical image using a trained classifier.

27. The apparatus of claim 26, wherein the trained classifier is a probabilistic boosting tree (PBT) classifier, and the other image based-features are Haar wavelet features.

28. A non-transitory computer readable medium storing computer program instructions for anatomical object detection in a 3D medical image of a patient, the computer program instructions when executed by a processor cause the processor to perform operations comprising:

receiving a 3D medical image of a patient including a target anatomical object; and detecting a 3D pose of the target anatomical object in the 3D medical image in a series of marginal parameter spaces of increasing dimensionality using a respective trained sparse deep neural network for each of the marginal parameter spaces, wherein each respective trained sparse deep neural network inputs hypothesis image patches in the respective marginal parameter space, samples voxels in each hypothesis image patch in a sparse sampling pattern adaptively learned during training of the respective trained sparse deep neural network, and calculates, for each hypothesis image patch, a probability that the hypothesis image patch is an image patch of the target anatomical object in the respective marginal parameter space based on the voxels sampled in the hypothesis image patch in the sparse sampling pattern.

29. The non-transitory computer readable medium of claim 28, wherein at least one of the respective trained sparse deep neural networks is trained by:

training a deep neural network by learning parameters of a respective filter for each of a plurality of neurons in each of a plurality of layers of the deep neural network, wherein the parameters of each respective filter include a bias and a plurality of weights that weight node outputs of the nodes of a previous one of the plurality of layers; and sparsifying the weights of the filters for at least one layer of the trained deep neural network.

30. The non-transitory computer readable medium of claim 29, wherein sparsifying the weights of the filters for at least one layer of the trained deep neural network comprises:

reducing a number of non-zero weights in each filter for the at least one layer in the trained deep neural network by setting a predetermined percentage of non-zero weights with lowest magnitudes in each filter equal to zero; and retraining the deep neural network with only the remaining non-zero weights in each filter for the at least one layer to refine the bias and the remaining non-zero weights in each filter for the at least one layer to recover from an effect of reducing the number of non-zero weights.

31. The non-transitory computer readable medium of claim 30, wherein sparsifying the weights of the filters for at least one layer of the trained deep neural network further comprises:

repeating the reducing and retraining steps in each of a plurality of iterations.

32. The non-transitory computer readable medium of claim 31, wherein sparsifying the weights of the filters for at least one layer of the trained deep neural network further comprises:

performing, in each iteration, a normalization to preserve an $L_1$-norm for each filter for the at least one layer.

33. The non-transitory computer readable medium of claim 31, wherein repeating the reducing and retraining steps in each of a plurality of iterations comprises:

repeating the reducing and retraining steps until a target sparsity degree is reached.

34. The non-transitory computer readable medium of claim 29, wherein the at least one layer is a first hidden layer of the deep neural network.

35. The non-transitory computer readable medium of claim 29, wherein sparsifying the weights of the filters for at least one layer of the trained deep neural network comprises:

performing re-weighted L1-norm regularization on the weights of the filters for the at least one layer of the trained deep neural network, wherein the re-weighted L1-norm regularization drives a plurality of non-zero weights of the filters for the at least one layer to zero; and training a sparse deep neural with only the remaining non-zero weights in the filters for the at least one layer.

36. The non-transitory computer readable medium of claim 28, wherein detecting a 3D pose of the target anatomical object in the 3D medical image in a series of marginal parameter spaces of increasing dimensionality using a respective trained sparse deep neural network for each of the marginal parameter spaces comprises, for each of the marginal parameter spaces:

filtering hypothesis image patches in that marginal parameter space using a respective cascade of trained shallow sparse neural networks to eliminate a plurality of negative hypothesis image patches; and evaluating each of the remaining hypothesis image patches in that marginal parameter space using the respective trained sparse deep neural network to determine a classification score for each of the remaining hypothesis image patches in that marginal parameter space.

37. The non-transitory computer readable medium of claim 36, wherein the respective cascade of trained shallow sparse neural networks for each marginal parameter space is trained by sequentially adding shallow sparse neural networks to the cascade until a balanced set of positive and negative training samples is achieved for training the respective sparse deep neural network.

38. The non-transitory computer readable medium of claim 28, further comprising:

rigidly registering a mean model of the target anatomical object to the 3D medical mage using the detected 3D pose of the target anatomical object in the 3D medical image;

refining the model of the target anatomical structure in the 3D medical image using a trained sparse deep neural network boundary detector applied to image patches corresponding to sampling points along a line normal to a surface of the model at each point on the surface of the model; and projecting the refined model of the target anatomical object in the 3D medical image to a learned shape space of the target anatomical object.

39. The non-transitory computer readable medium of claim 28, wherein the series of marginal parameter spaces comprises a position parameter space, a position-orientation parameter space, and a position-orientation-scale parameter space.

40. The non-transitory computer readable medium of claim 39, wherein detecting a 3D pose of the target anatomical object in the 3D medical image in a series of marginal parameter spaces of increasing dimensionality using a respective trained sparse deep neural network for each of the marginal parameter spaces comprises:

detecting position candidates in the 3D medical image using a first cascade of trained sparse shallow neural networks to filter image patches centered at each of a plurality of voxels in the medical image and a first trained sparse deep neural network to evaluate image patches not eliminated by the first cascade;

generating position-orientation hypotheses based on the detected position candidates;

detecting position-orientation candidates in the 3D medical image using a second cascade of trained sparse shallow neural networks to filter image patches corresponding to the position-orientation hypotheses and a second trained sparse deep neural network to evaluate image patches corresponding position-orientation hypotheses not eliminated by the second cascade;

generating position-orientation-scale hypotheses based on the detected position-orientation candidates; and detecting the pose of the target anatomical object in the 3D medical image using a third cascade of trained sparse shallow neural networks to filter image patches corresponding to the position-orientation-scale hypotheses and a third trained sparse deep neural network to evaluate image patches corresponding position-orientation-scale hypotheses not eliminated by the third cascade.

41. A non-transitory computer readable medium storing computer program instruction for automated anatomical landmark detection in a 3D medical image, the computer program instructions when executed by a processor cause the processor to perform operations comprising:

detecting a plurality of landmark candidates for a target anatomical landmark in the 3D medical image using an initial shallow neural network detector;

calculating deeply learned features for each of the plurality of landmark candidates using a trained deep neural network, wherein the trained deep neural network inputs respective image patches for the plurality of landmark candidates, samples voxels in each respective image patch in a sparse sampling pattern adaptively learned during training of the trained deep neural network, and calculates the deeply learned features for the plurality of landmark candidates based on the voxels sampled in the respective image patches in the sparse sampling pattern; and detecting the target anatomical landmark in the 3D medical image from the plurality of landmark candidates based on the deeply learned features for each of the plurality of landmark candidates and other image-based features extracted from the 3D medical image using a trained classifier.

42. The non-transitory computer readable medium of claim 41, wherein the trained classifier is a probabilistic boosting tree (PBT) classifier, and the other image based-features are Haar wavelet features.

* * * * *